United States Patent
Sasaki

(10) Patent No.: US 10,070,771 B2
(45) Date of Patent: Sep. 11, 2018

(54) IMAGE PROCESSING APPARATUS, METHOD FOR OPERATING IMAGE PROCESSING APPARATUS, COMPUTER-READABLE RECORDING MEDIUM, AND ENDOSCOPE DEVICE

(71) Applicant: OLYMPUS CORPORATION, Tokyo (JP)

(72) Inventor: Hiroshi Sasaki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/637,422

(22) Filed: Jun. 29, 2017

(65) Prior Publication Data
US 2017/0296034 A1    Oct. 19, 2017

Related U.S. Application Data

(63) Continuation of application No. PCT/JP2015/050400, filed on Jan. 8, 2015.

(51) Int. Cl.
*H04N 9/07* (2006.01)
*H04N 9/083* (2006.01)
(Continued)

(52) U.S. Cl.
CPC ...... *A61B 1/00013* (2013.01); *A61B 1/00009* (2013.01); *G02B 23/2461* (2013.01);
(Continued)

(58) Field of Classification Search
CPC ........... H04N 2209/046; H04N 5/3458; H04N 5/3537; H04N 7/183; H04N 2005/2255;
(Continued)

(56) References Cited

U.S. PATENT DOCUMENTS

| 6,480,300 B1 * | 11/2002 | Aoyama | G06T 5/004 358/1.9 |
| 6,724,932 B1 * | 4/2004 | Ito | G06T 3/4015 348/275 |

(Continued)

FOREIGN PATENT DOCUMENTS

| CN | 102151118 A | 8/2011 |
| JP | 2005-333418 A | 12/2005 |

(Continued)

OTHER PUBLICATIONS

International Search Report dated Apr. 7, 2015 issued in PCT/JP2015/050400.

*Primary Examiner* — Chia-Wei A Chen
(74) *Attorney, Agent, or Firm* — Scully, Scott, Murphy & Presser, P.C.

(57) ABSTRACT

An image processing apparatus interpolates a signal of a missing color component based on first, second, and third color signals respectively generated by first, second, and third pixels of an image sensor, to generate color signals. These pixels are arranged in a matrix. The first pixels generate the first color signal of a first luminance component of white light. The second pixels generate the second color signal of a second luminance component of narrow band light. Density of the first pixels being higher than density of the second pixels and density of the third pixels. The apparatus extracts a specific frequency component signal from a color signal of the first luminance component among the color signals generated by interpolation, and adds the specific frequency component signal to a color signal of a color component different from the first luminance component depending on white light imaging or narrow band imaging.

10 Claims, 15 Drawing Sheets

(51) Int. Cl.
   *H04N 3/14*      (2006.01)
   *H04N 5/335*     (2011.01)
   *H04N 9/04*      (2006.01)
   *A61B 1/00*      (2006.01)
   *G02B 23/24*     (2006.01)
   *G06T 7/00*      (2017.01)
   *G06T 7/11*      (2017.01)

(52) U.S. Cl.
   CPC ............... *G06T 7/0012* (2013.01); *G06T 7/11* (2017.01); *G06T 2207/20036* (2013.01)

(58) Field of Classification Search
   CPC ......... G06T 3/4015; G06T 2207/20036; G06T 7/0012; G06T 7/11; G02B 23/2461; A61B 1/00009; A61B 1/00013
   See application file for complete search history.

(56) References Cited

U.S. PATENT DOCUMENTS

| | | | |
|---|---|---|---|
| 8,452,092 B2 | 5/2013 | Sasaki | |
| 2003/0081117 A1* | 5/2003 | Bogdanowicz | H04N 5/253 348/97 |
| 2003/0081177 A1* | 5/2003 | Rosen | H04N 5/253 352/38 |
| 2005/0094007 A1* | 5/2005 | Nomura | H04N 9/045 348/272 |
| 2009/0149706 A1 | 6/2009 | Yamazaki et al. | |
| 2011/0043657 A1* | 2/2011 | Hara | H04N 9/045 348/223.1 |
| 2011/0122273 A1* | 5/2011 | Kanemitsu | H04N 9/045 348/222.1 |
| 2011/0176730 A1* | 7/2011 | Sasaki | G06T 3/4015 382/167 |
| 2012/0212643 A1* | 8/2012 | Kanemitsu | H04N 9/045 348/223.1 |
| 2013/0182002 A1* | 7/2013 | Macciola | H04N 1/387 345/589 |
| 2013/0286262 A1* | 10/2013 | Hayashi | H04N 9/045 348/280 |
| 2015/0042782 A1* | 2/2015 | Koga | G02B 21/367 348/79 |
| 2015/0363912 A1* | 12/2015 | Elliott | G06T 3/4015 348/277 |
| 2017/0280122 A1* | 9/2017 | Sato | H04N 9/77 |

FOREIGN PATENT DOCUMENTS

| | | |
|---|---|---|
| JP | 2006-068113 A | 3/2006 |
| JP | 2008-043604 A | 2/2008 |
| JP | 2011-143100 A | 7/2011 |
| JP | 2012-170640 A | 9/2012 |
| JP | 2014-039105 A | 2/2014 |

* cited by examiner

FIG.3

| $P_{11}$ | $P_{12}$ | $P_{13}$ | $P_{14}$ | ... |
|---|---|---|---|---|
| $P_{21}$ | $P_{22}$ | $P_{23}$ | $P_{24}$ | ... |
| $P_{31}$ | $P_{32}$ | $P_{33}$ | $P_{34}$ | ... |
| $P_{41}$ | $P_{42}$ | $P_{43}$ | $P_{44}$ | ... |
| ⋮ | ⋮ | ⋮ | ⋮ | ⋱ |

| $R_{11}$ | $G_{12}$ | $R_{13}$ | $G_{14}$ | ... |
|---|---|---|---|---|
| $G_{21}$ | $B_{22}$ | $G_{23}$ | $B_{24}$ | ... |
| $R_{31}$ | $G_{32}$ | $R_{33}$ | $G_{34}$ | ... |
| $G_{41}$ | $B_{42}$ | $G_{43}$ | $B_{44}$ | ... |
| ⋮ | ⋮ | ⋮ | ⋮ | ⋱ |

FIG.10

| (B-G)$_{11}$ |  | (B-G)$_{13}$ |  | ... |
|---|---|---|---|---|
|  | (R-G)$_{22}$ |  | (R-G)$_{24}$ | ... |
| (B-G)$_{31}$ |  | (B-G)$_{33}$ |  | ... |
|  | (R-G)$_{42}$ |  | (R-G)$_{44}$ | ... |
| ⋮ | ⋮ | ⋮ | ⋮ | ⋱ |

FIG.11

|  | $f_{B-G}(k,l-2)$ |  | $f_{B-G}(k+2,l-2)$ |
|---|---|---|---|
| $f_{B-G}(k-1,l-1)$ |  | $f_{B-G}(k+1,l-1)$ |  |
|  | $f_{B-G}(k,l)$ |  | $f_{B-G}(k+2,l)$ |
| $f_{B-G}(k-1,l+1)$ |  | $f_{B-G}(k+1,l+1)$ |  |

# IMAGE PROCESSING APPARATUS, METHOD FOR OPERATING IMAGE PROCESSING APPARATUS, COMPUTER-READABLE RECORDING MEDIUM, AND ENDOSCOPE DEVICE

CROSS REFERENCES TO RELATED APPLICATIONS

This application is a continuation of PCT international application Ser. No. PCT/JP2015/050400, filed on Jan. 8, 2015 which designates the United States, incorporated herein by reference.

BACKGROUND

1. Technical Field

The disclosure relates to an image processing apparatus for performing signal processing on an imaging signal generated by an image sensor to generate an image signal. The disclosure also relates to a method for operating the image processing apparatus, a computer-readable recording medium, and an endoscope device including the image processing apparatus.

2. Related Art

In the related art, endoscope devices have been widely used for various tests in the medical field and the industrial field. Of these, endoscope devices for medical use are popular since they are capable of acquiring an in-vivo image of a subject without incising the subject by inserting, into the subject such as a patient, an elongate flexible insertion unit provided with an image sensor including a plurality of pixels at a distal end thereof, thereby placing less burden on the subject.

As observation methods of such an endoscope device, a white light imaging using white illumination light and a narrow band imaging using illumination light of a narrow band which is a wavelength band narrower than that of white light (narrow band illumination light) are widely known. Of these, the narrow band imaging allows for obtaining an image where capillaries, a fine pattern of the mucosa, etc. present in the mucosal surface layer of a living body (biological surface layer) for example are displayed in an enhanced manner. According to the narrow band imaging, a lesioned part in the mucosal surface layer of a living body can be detected more accurately. Regarding such imaging methods of endoscope devices, it is desired to perform observation while the white light imaging and the narrow band imaging are switched.

As technique to perform observation by switching between the white light imaging and the narrow band imaging, proposed is an endoscope system capable of switching between a white light imaging mode where illumination light of the three primary colors of R, G, and B are sequentially emitted onto tissues in a subject and a white light image is generated from reflection light thereof and a narrow band imaging mode where illumination light formed by two types of narrow band light included in wavelength bands of blue light and green light are sequentially emitted and a narrow band image is generated from reflection light thereof (e.g. JP 2006-68113 A). The two types of narrow band light included in the wavelength bands of blue light and green light each have different absorption characteristics by hemoglobin in the blood vessels and different attenuation amounts in a depth direction in a living body according to the wavelength. In a special light image, capillaries in a surface layer and a mucosa structure in a surface layer can be captured by narrow band light included in the wavelength band of blue light and thicker blood vessels in a deeper layer can be captured by narrow band light included in the wavelength band of green light.

In order to generate and display a color image by the imaging method described above, a color filter of a Bayer array is provided on a light-receiving surface of an image sensor of a single plate to acquire images. In such a Bayer filter, four filters respectively passing red (R) wavelength band light, green (G) wavelength band light, green (G) wavelength band light, and blue (B) wavelength band light are arrayed as one unit for each of pixels. In this filter, each of the pixels receives light of a wavelength band passed through the filter to generate an electric signal of a color component according to a color of that wavelength band. In order to generate a color image, therefore, interpolation processing is performed for interpolating a signal value of a missing color component that has not passed through the filter in each of the pixels. Such interpolation processing is called demosaicking processing. Hereinafter, a signal acquired by a G pixel (This refers to a pixel on which a G filter is arranged. An R pixel and a B pixel are defined likewise.) is referred to as a G signal (an R signal in the case of an R pixel and a B signal in the case of a B pixel).

As an example of demosaicking processing, proposed is technique to interpolate a G signal in an R pixel and a B pixel that lack a G signal by utilizing correlation with surrounding G pixels and, with respect to a color difference signal (R-G signal and B-G signal) calculated using an R signal of an R pixel or a B signal of a B pixel position, to interpolate a color difference signal to a pixel position lacking a color difference signal using the correlation with the surrounding G pixels that have been used upon interpolation of the G signal (e.g. see JP 2005-333418 A).

When demosaicking processing is performed based on electric signals obtained by a Bayer array, a high resolution can be ensured in the white light imaging by performing interpolation processing using signal values of G pixels. In the narrow band imaging, however, there are cases where a high resolution image cannot be obtained even when interpolation processing similar to the above is performed since color correlation between a G pixel and a B pixel is low.

As technique to obtain an image based on blue narrow band light, an endoscope device that emits white illumination light and narrow band illumination light of a narrow band included in a blue wavelength band is disclosed (e.g. see JP 2012-170640 A). In JP 2012-170640 A, it is regarded that a G pixel has slight sensitivity to blue narrow band light and, from a G signal, a B signal, and an R signal obtained from the above illumination light, a B signal component corresponding to blue narrow band light captured at the G pixel is extracted from correlation operation between the G signal and the R signal. Combining the extracted B signal component and a B signal generated from a B pixel based on blue narrow band light results in generation of an enhanced image of capillaries in a surface layer.

SUMMARY

In some embodiments, provided is an image processing apparatus for interpolating a signal of a missing color component based on first, second, and third color signals respectively generated by first, second, and third pixels of an image sensor, to generate an image signal having color signals of color components, the first, second, and third pixels being arranged in a matrix, the first pixels being configured to generate the first color signal of a first luminance component that is a luminance component of white illumination light including red wavelength band light, green wavelength band light, and blue wavelength band light, the second pixels being configured to generate the second color signal of a second luminance component that is a luminance component of narrow band illumination light having a wavelength band narrower than a wavelength band of the white illumination light, and the third pixels being configured to generate the third color signal of a color component different from the first and the second luminance components, a density of the first pixels being higher than each of a density of the second pixels and a density of the third pixels. The image processing apparatus includes: a specific frequency component extracting unit configured to extract a specific frequency component signal having a predetermined spatial frequency component, from a color signal of the first luminance component among the color signals of the color components generated by interpolation; and a specific frequency component addition unit configured to add the specific frequency component signal extracted by the specific frequency component extracting unit to a color signal of a color component different from the first luminance component determined depending on an imaging method by the white illumination light or an imaging method by the narrow band illumination light.

In some embodiments, provided is a method for operating an image processing apparatus for interpolating a signal of a missing color component based on first, second, and third color signals respectively generated by first, second, and third pixels of an image sensor, to generate an image signal having color signals of color components, the first, second, and third pixels being arranged in a matrix, the first pixels being configured to generate the first color signal of a first luminance component that is a luminance component of white illumination light including red wavelength band light, green wavelength band light, and blue wavelength band light, the second pixels being configured to generate the second color signal of a second luminance component that is a luminance component of narrow band illumination light having a wavelength band narrower than a wavelength band of the white illumination light, and the third pixels being configured to generate the third color signal of a color component different from the first and the second luminance components, a density of the first pixels being higher than each of a density of the second pixels and a density of the third pixels. The method includes: extracting, by a specific frequency component extracting unit, a specific frequency component signal having a predetermined spatial frequency component, from a color signal of the first luminance component among the color signals of the color components generated by interpolation; and adding, by a specific frequency component addition unit, the specific frequency component signal extracted by the specific frequency component extracting unit to a color signal of a color component different from the first luminance component determined depending on an imaging method by the white illumination light or an imaging method by the narrow band illumination light.

In some embodiments, provided is a non-transitory computer-readable recording medium with an executable program stored thereon for operating an image processing apparatus for interpolating a signal of a missing color component based on first, second, and third color signals respectively generated by first, second, and third pixels of an image sensor, to generate an image signal having color signals of color components, the first, second, and third pixels being arranged in a matrix, the first pixels being configured to generate the first color signal of a first luminance component that is a luminance component of white illumination light including red wavelength band light, green wavelength band light, and blue wavelength band light, the second pixels being configured to generate the second color signal of a second luminance component that is a luminance component of narrow band illumination light having a wavelength band narrower than a wavelength band of the white illumination light, and the third pixels being configured to generate the third color signal of a color component different from the first and the second luminance components, a density of the first pixels being higher than each of a density of the second pixels and a density of the third pixels. The program causes the image processing apparatus to execute: extracting, by a specific frequency component extracting unit, a specific frequency component signal having a predetermined spatial frequency component, from a color signal of the first luminance component among the color signals of the color components generated by interpolation; and adding, by a specific frequency component addition unit, the specific frequency component signal extracted by the specific frequency component extracting unit to a color signal of a color component different from the first luminance component determined depending on an imaging method by the white illumination light or an imaging method by the narrow band illumination light.

In some embodiments, an endoscope device includes: a light source unit configured to emit one of white illumination light and narrow band illumination light, the white illumination light including red wavelength band light, green wavelength band light, and blue wavelength band light, the narrow band illumination light having a wavelength band narrower than a wavelength band of the white illumination light; an image sensor in which first, second, and third pixels are arranged in a matrix, the first pixels being configured to generate a first color signal of a first luminance component that is a luminance component of the white illumination light, the second pixels being configured to generate a second color signal of a second luminance component that is a luminance component of the narrow band illumination light, and the third pixels being configured to generate a third color signal of a color component different from the first and the second luminance components, a density of the first pixels being higher than each of a density of the second pixels and a density of the third pixels; and the image processing apparatus.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 3 is a schematic diagram illustrating a configuration of pixels of an image sensor according to the embodiment of the present invention;

FIG. 4 is a schematic diagram illustrating an exemplary configuration of a color filter according to the embodiment of the present invention;

FIG. 10 is a schematic diagram explaining demosaicking processing performed by the processor according to the embodiment of the present invention;

FIG. 11 is a schematic diagram explaining the demosaicking processing performed by the processor according to the embodiment of the present invention;

DETAILED DESCRIPTION

Exemplary embodiments of the present invention will be described below. In the embodiments, reference will be made to an endoscope device for medical use that includes an image processing apparatus according to the present invention and captures and display in-vivo images of a patient or the like. The present invention is not limited by the embodiments. The same reference signs are used to designate the same elements throughout the drawings.

In the embodiment below, a partial wavelength band out of a wavelength band of light forming white light is described as a "narrow band". The narrow band is not required to be a range narrower than the wavelength band of white light and may include a wavelength band out of the range of the wavelength band of white light (visible light) (e.g. infrared, ultraviolet, etc.).

Embodiments

Figure 1:
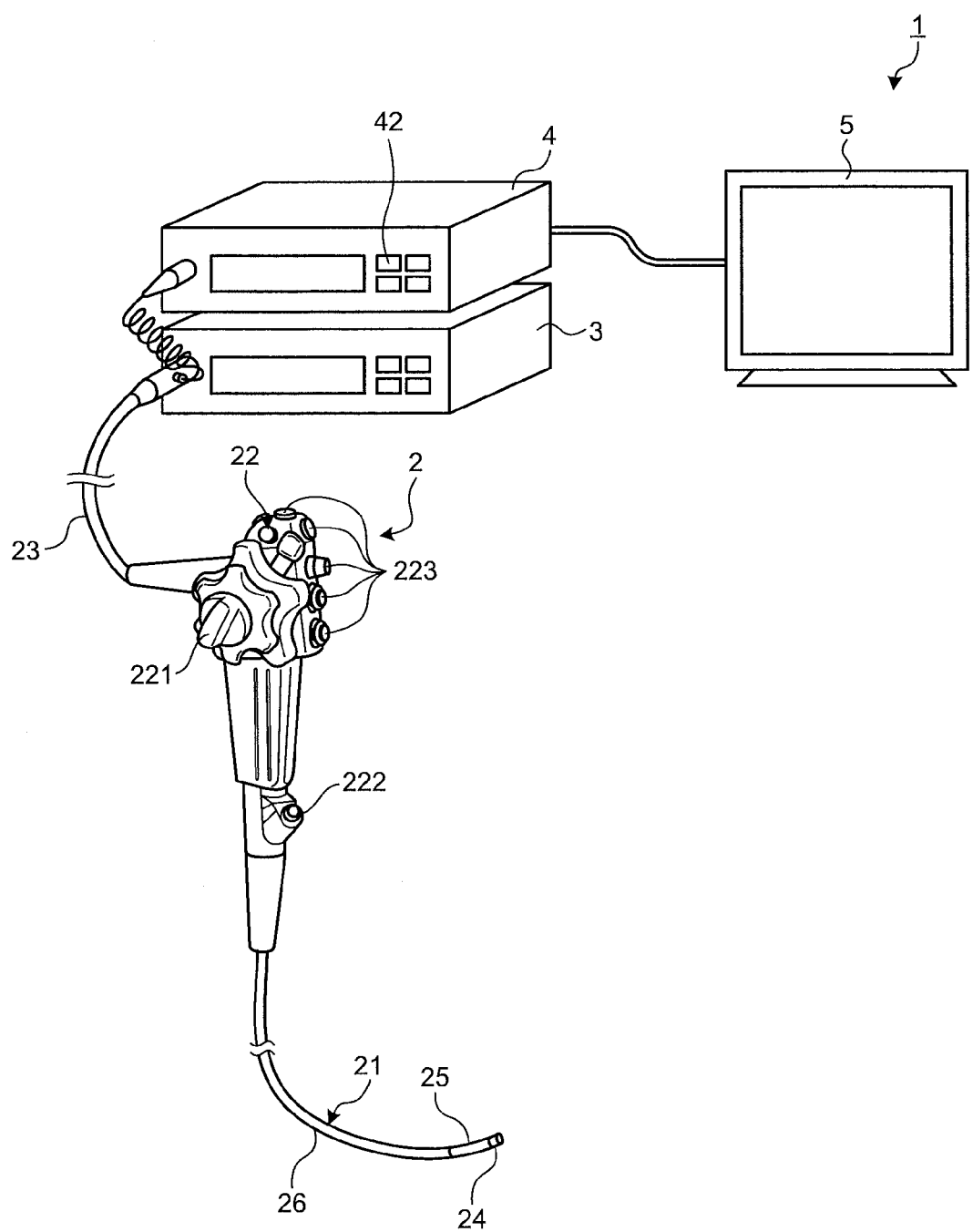
FIG. 1 is a diagram illustrating a schematic configuration of an endoscope device according to an embodiment of the present invention.
Figure 2:
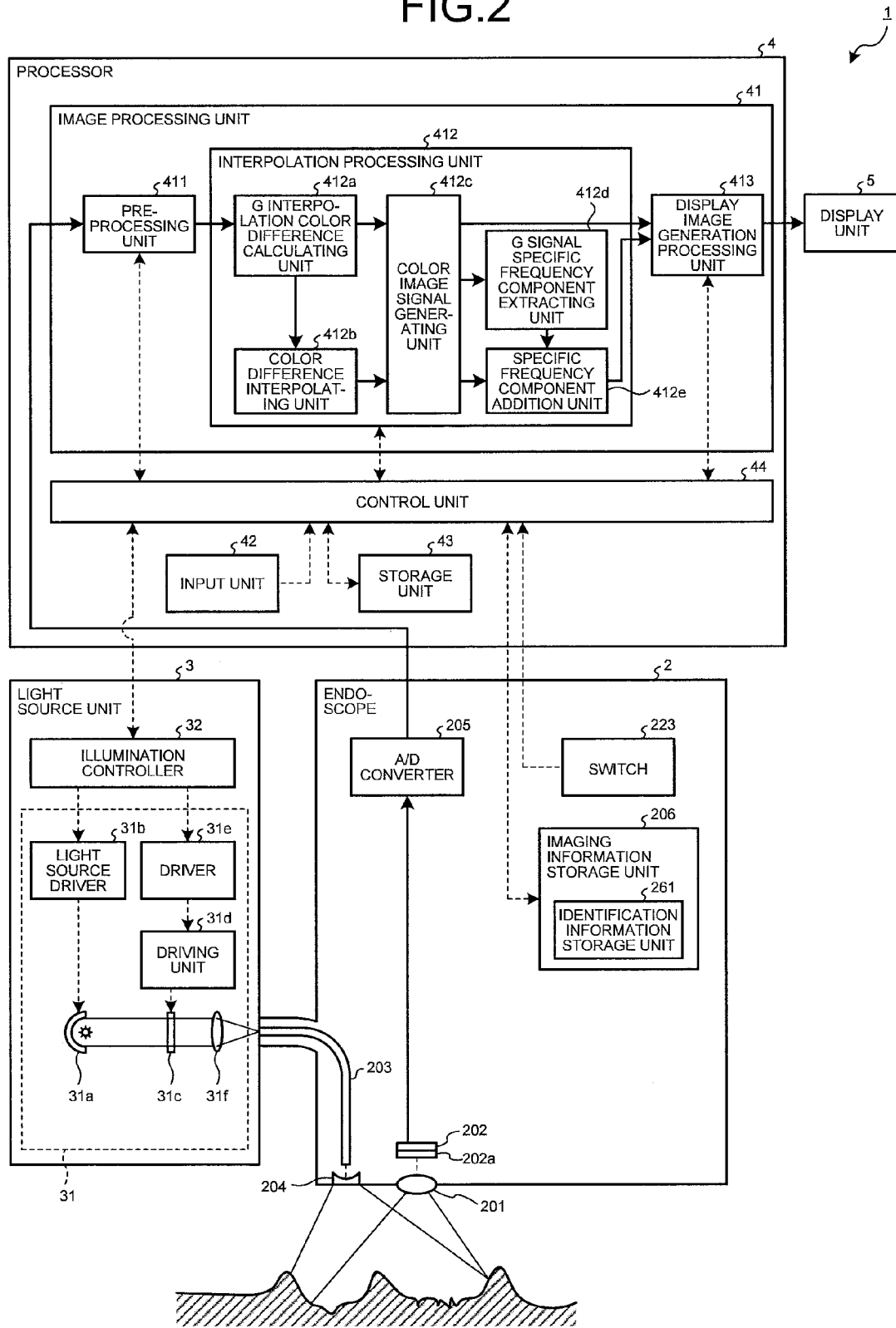
FIG. 2 is a schematic diagram illustrating a schematic configuration of the endoscope device according to the embodiment of the present invention.

FIG. 1 is a diagram illustrating a schematic configuration of an endoscope device 1 according to an embodiment of the present invention. FIG. 2 is a schematic diagram illustrating a schematic configuration of the endoscope device 1 according to the embodiment of the present invention. An endoscope device 1 illustrated in FIGS. 1 and 2 includes: an endoscope 2 has an insertion unit 21 to be inserted into a subject to capture in-vivo images of an observed region and generates an electric signal; a light source unit 3 that generates illumination light to be emitted from a distal end of the endoscope 2; a processor 4 that performs predetermined image processing on the electric signal acquired by the endoscope 2 and performs overall control of the endoscope device 1; and a display unit 5 that displays the in-vivo images after the image processing by the processor 4. The endoscope device 1 acquires the in-vivo images of the subject by insertion of the insertion unit 21 into the subject such as a patient. An operator such as a doctor observes the acquired in-vivo images to examine whether there is a bleeding site or a tumor site to be detected.

The endoscope 2 includes: the insertion unit 21 that is flexible and has a long thin shape; an operating unit 22 connected to a proximal end side of the insertion unit 21 and receives input of various operation signals; and a universal cord 23 extending in a different direction from a direction in which the insertion unit 21 extends from the operating unit 22 and incorporates various cables connected to the light source unit 3 and the processor 4.

The insertion unit 21 includes: a distal end part 24 having an image sensor 202 in which pixels (photodiodes) are arranged in a matrix for receiving light and performing photoelectric conversion on the received light to generate an image signal; a bending portion 25 bendable and formed by a plurality of bending pieces; and an elongate flexible tube portion 26 connected to a proximal end side of the bending portion 25.

The operating unit 22 includes: a bending knob 221 that causes the bending portion 25 to bend in the vertical direction and the horizontal direction; a treatment tool insertion portion 222 through which a treatment tool, such as biopsy forceps, an electric scalpel, and an inspection probe, is configured to be inserted into a subject; and a plurality of switches 223 for inputting a command signal for causing the light source unit 3 to perform switching operation of illumination light, an operation command signal for an external device connected to a treatment tool or the processor 4, a water supply command signal for supplying water, a suction command signal for performing suction, or other command signals. A treatment tool inserted from the treatment tool insertion portion 222 is exposed from an opening part (not illustrated) via a treatment tool channel (not illustrated) included in a distal end of the distal end part 24.

The universal cord 23 incorporates at least a light guide 203 and a collective cable where one or more signal wires are bundled. The collective cable includes signal wires for transmitting and receiving a signal to and from the endoscope 2, the light source unit 3, and the processor 4 including a signal wire for transmitting and receiving setting data, a signal wire for transmitting and receiving an image signal, a signal wire for transmitting and receiving a timing signal for driving the image sensor 202, and other signal wires.

The endoscope 2 includes an imaging optical system 201, the image sensor 202, the light guide 203, an illumination lens 204, an A/D converter 205, and an imaging information storage unit 206.

The imaging optical system 201 is provided to the distal end part 24 and concentrates light at least from an observed region. The imaging optical system 201 is formed by one or more lenses. The imaging optical system 201 may be provided with an optical zoom mechanism that changes the angle of view and a focus mechanism that changes the focus.

The image sensor 202 is disposed vertically with respect to an optical axis of the imaging optical system 201 and generates an electric signal (image signal) by photoelectric conversion of an image of light formed by the imaging optical system 201. The image sensor 202 is implemented by using a charge coupled device (CCD) image sensor, a complementary metal oxide semiconductor (CMOS) image sensor, or other sensors.

FIG. 3 is a schematic diagram illustrating a configuration of pixels of the image sensor 202. The image sensor 202 has the plurality of pixels arranged in a matrix to receive light from the imaging optical system 201. The image sensor 202 further generates an electric signal (also referred to as an image signal) by performing photoelectric conversion on light received by each of the pixels. This electric signal includes a pixel value (luminance value) of each of the pixels, positional information of the pixels, or other information. In FIG. 3, a pixel arranged in a column i and a row j is denoted as pixel $P_{ij}$ (where i and j are natural numbers).

The image sensor 202 includes a color filter 202a provided between the imaging optical system 201 and the image sensor 202 and having a plurality of filters, each of which is configured to pass light of a individually defined wavelength band. The color filter 202a is included on a light-receiving surface of the image sensor 202.

FIG. 4 is a schematic diagram illustrating an exemplary configuration of the color filter 202a. In the color filter 202a, filter units U1, each formed by four filters aligned in 2×2 matrix, are disposed in a matrix corresponding arrangement of a pixel $P_{ij}$. In other words, a filter array of the filter unit U1 is regarded as a basic pattern and that basic pattern is arranged repeatedly in the color filter 202a. On a light-receiving surface of each of the pixels, one filter for passing light of a predetermined wavelength band is arranged. Therefore the pixel $P_{ij}$ provided with the filter receives light of the wavelength band passed through the filter. For example, a pixel $P_{ij}$, on which a filter for passing light of a green wavelength band is provided, receives light of the green wavelength band. Hereinbelow a pixel $P_{ij}$ for receiving light of the green wavelength band is referred to as a G pixel. Similarly, a pixel for receiving light of a blue wavelength band is referred to as a B pixel and a pixel for receiving light of a red wavelength band is referred to as an R pixel.

The filter unit U1 passes light of the blue (B) wavelength band $H_B$, the green (G) wavelength band $H_G$, and the red (R) wavelength band $H_R$. Furthermore, the filter unit U1 is formed by a blue filter (B filter) for passing light of the wavelength band $H_B$, a green filter (G filter) for passing light of the wavelength band $H_G$, a red filter (R filter) for passing light of the wavelength band $H_R$. The two G filters are arranged diagonally while the B filter and the R filter are arranged diagonally, thereby forming a so-called Bayer array. In the filter unit U1, the density of the G filters is higher than the density of the B filters or the R filters. In other words, the density of the G pixels is higher than the density of the B pixels or the R pixels in the image sensor 202. The blue, green, and red wavelength bands $H_B$, $H_G$, and $H_R$ are for example 380 nm to 500 nm, 480 nm to 600 nm, and 580 nm to 650 nm, respectively.

Returning to descriptions on FIGS. 1 and 2, the light guide 203 is formed by a glass fiber or the like and thereby forms a light guiding path of light emitted by the light source unit 3.

The illumination lens 204 is provided to a distal end of the light guide 203 and diffuses light guided by the light guide 203 and emits the light outside the distal end part 24.

The A/D converter 205 performs A/D conversion on the electric signal generated by the image sensor 202 and outputs the converted electric signal to the processor 4. The A/D converter 205 converts the electric signal generated by the image sensor 202 into digital data (image signal) of twelve bits, for example.

The imaging information storage unit 206 stores data including various programs for causing the endoscope 2 to operate, various parameters required for operation of the endoscope 2, an identification information of the endoscope 2. Moreover, the imaging information storage unit 206 includes an identification information storage unit 261 that stores identification information. Identification information includes specific information (ID) of the endoscope 2, year of manufacture, specification information, transmission method, information on filter array of the color filter 202a, etc. The imaging information storage unit 206 is implemented by a flash memory or the like.

Next, a configuration of the light source unit 3 will be described. The light source unit 3 includes an illumination unit 31 and an illumination controller 32.

The illumination unit 31 switches between a plurality of rays of illumination light having different wavelength bands, and emits the illumination light under control by the illumination controller 32. The illumination unit 31 includes a light source 31a, a light source driver 31b, a switching filter 31c, a driving unit 31d, a driver 31e, and a condenser lens 31f.

The light source 31a emits white illumination light including light of the red, the green, and the blue wavelength bands $H_R$, $H_G$, $H_B$ under control by the illumination controller 32. White illumination light generated by the light source 31a is emitted outside the distal end part 24 via the switching filter 31c, the condenser lens 31f, and the light guide 203. The light source 31a is implemented by a light source that emits white light such as a white LED or a xenon lamp.

The light source driver 31b supplies a current to the light source 31a under control by the illumination controller 32 and thereby causes the light source 31a to emit white illumination light.

The switching filter 31c passes only blue narrow band light and green narrow band light the out of white illumination light emitted by the light source 31a. The switching filter 31c is disposed on an optical path of white illumination light emitted by the light source 31a in a freely insertable and removable manner under control by the illumination controller 32. The switching filter 31c passes only two types of narrow band light when disposed on the optical path of white illumination light. Specifically, the switching filter 31c passes narrow band illumination light formed by light of a narrow band $T_B$ (e.g. 400 nm to 445 nm) included in the wavelength band $H_B$ and light of a narrow band $T_G$ (e.g. 530 nm to 550 nm) included in the wavelength band $H_G$. These narrow bands $T_B$ and $T_G$ are wavelength bands of blue light and green light that are likely to be absorbed by hemoglobin in the blood. The narrow band $T_B$ is only required to include at least 405 nm to 425 nm. Light emitted while limited to these bands is referred to as narrow band illumination light and imaging by the narrow band illumination light is referred to as a narrow band imaging (NBI).

The driving unit 31d is formed by a stepping motor, a DC motor, or other motors and causes the switching filter 31c to be inserted to or removed from the optical path of the light source 31a.

The driver 31e supplies a predetermined current to the driving unit 31d under control by the illumination controller 32.

The condenser lens 31f collects white illumination light emitted by the light source 31a or narrow band illumination light passed through the switching filter 31c, and emits the light outside the light source unit 3 (to the light guide 203).

The illumination controller 32 controls the light source driver 31b to cause on/off operation of the light source 31a and controls the driver 31e to cause the switching filter 31c to be inserted to or removed from the optical path of the light source 31a, thereby controlling the type (band) of illumination light emitted by the illumination unit 31.

Specifically, the illumination controller 32 causes the switching filter 31c to be inserted to or removed from the optical path of the light source 31a and thereby performs control of switching illumination light emitted by the illumination unit 31 to one of white illumination light and narrow band illumination light. In other words, the illumination controller 32 performs control of switching to one of the white light imaging (WLI) using white illumination light including light of the wavelength bands $H_B$, $H_G$, and $H_R$ and the narrow band imaging (NBI) using narrow band illumination light formed by light of the narrow bands $T_B$ and $T_G$.

In the white light imaging (WLI), a green component (wavelength band $H_G$) forms a luminance component (first luminance component) while in the narrow band imaging (NBI) a blue component (narrow band $T_B$) forms a luminance component (second luminance component). In the image sensor 202 according to the embodiment, therefore, the G pixel corresponds to a first pixel, the B pixel corresponds to a second pixel, and the R pixel corresponds to a third pixel. A luminance component in the present invention refers to a color component forming the main component of a luminance signal Y in an XYZ colorimetric system for example, which will be described later. For example in the white light imaging, a green component that has the highest relative luminosity factor to human eyes and clearly draws blood vessels or gland duct structures of a living body forms a luminance component. In the narrow band imaging, a selected luminance component is different depending on a target. There may be cases where a green component is selected like in the white light imaging or cases where a luminance component is different from that in white light imaging. Specifically, representative examples where a blue component or a red component forms a luminance component in the narrow band imaging include the NBI described above. In this case, a blue component that clearly draws blood vessels or gland duct structures in a surface layer of a living body forms a luminance component. In the embodiment, a green component is regarded as the luminance component in the white light imaging and a blue component is regarded as the luminance component in the narrow band imaging.

Figure 5:
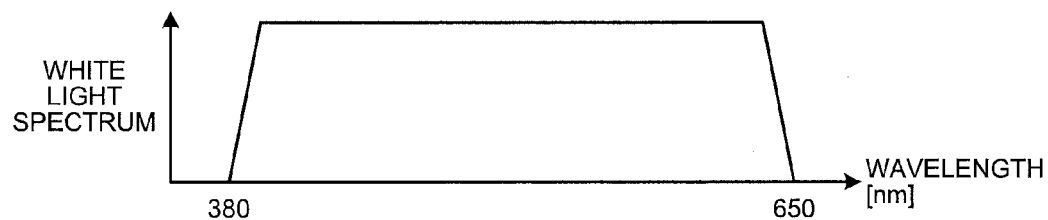
FIG. 5 is a graph illustrating relationship between the wavelength and the amount of light of illumination light emitted by an illumination unit of the endoscope device according to the embodiment of the present invention.
Figure 6:
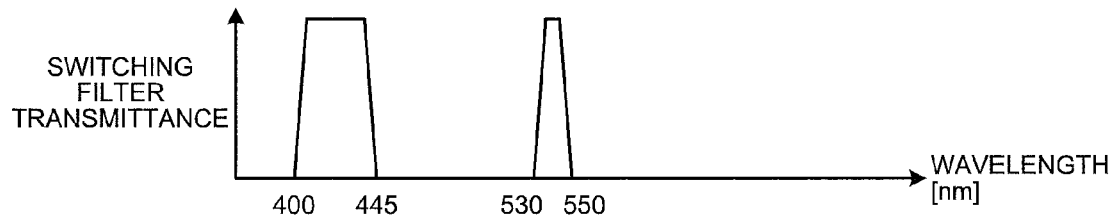
FIG. 6 is a graph illustrating relationship between the wavelength and the transmittance of illumination light through a switching filter included in the illumination unit of the endoscope device according to the embodiment of the present invention.

FIG. 5 is a graph illustrating relationship between the wavelength and the amount of light of illumination light emitted by the illumination unit 31. FIG. 6 is a graph illustrating relationship between the wavelength and the transmittance of illumination light through the switching filter 31c included in the illumination unit 31. When the switching filter 31c is removed from the optical path of the light source 31a by control by the illumination controller 32, the illumination unit 31 emits white illumination light including light of the wavelength bands $H_B$, $H_G$, and $H_R$ like a white light spectrum illustrated in FIG. 5. Contrary to this, when the switching filter 31c is inserted to the optical path of the light source 31a by control by the illumination controller 32, the illumination unit 31 emits narrow band illumination light including light of the narrow bands $T_B$ and $T_G$ (see FIG. 6).

Next, a configuration of the processor 4 will be described. The processor 4 includes an image processing unit 41, an input unit 42, a storage unit 43, and a control unit 44.

The image processing unit 41 executes predetermined image processing on the basis of the electric signal from the endoscope 2 (A/D converter 205) to generate image information to be displayed by the display unit 5. The image processing unit 41 includes a preprocessing unit 411, an interpolation processing unit 412, and a display image generation processing unit 413.

The preprocessing unit 411 performs optical black (OB) clamp processing, noise reduction (NR) processing, and white balance (WB) processing on the electric signal from the A/D converter 205 and outputs an image signal after the signal processing to the interpolation processing unit 412.

Figure 7:
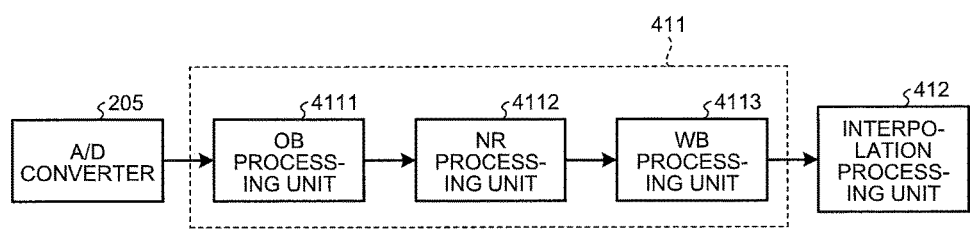
FIG. 7 is a block diagram explaining a configuration of a preprocessing unit of a processor according to the embodiment of the present invention.

FIG. 7 is a block diagram explaining a configuration of the preprocessing unit 411. The preprocessing unit 411 includes an OB processing unit 4111, an NR processing unit 4112, and a WB processing unit 4113.

The OB processing unit 4111 performs OB clamp processing on each of an R signal, a G signal, and a B signal of the image signal input from the A/D converter 205. In the OB clamp processing, an average value of a predetermined area corresponding to an optical black area is calculated based on the electric signal input from the endoscope 2 (A/D converter 205) and the average value is subtracted from the electric signal, thereby correcting the black level to a value zero.

The NR processing unit 4112 acquires, from the control unit 44, imaging method information indicating whether the current imaging method is WLI or NBI, modifies the amount of noise reduction according to the imaging method information, and performs noise reduction processing on the image signal applied with the OB clamp processing.

The WB processing unit 4113 performs, on the image signal applied with the noise reduction processing, white balance processing based on the imaging method information and outputs the image signal after the white balance processing to the interpolation processing unit 412. When signals of channels (color components) obtained by the narrow band imaging (NBI) are two (G signal and B signal), the WB processing unit 4113 performs balance correction processing on signals between the two channels while multiplying the remaining one channel (R signal in the first embodiment) with zero.

The interpolation processing unit 412 determines an interpolation direction from correlation of color information (pixel values) of a plurality of pixels based on the image signal input from the preprocessing unit 411 and performs interpolation based on color information of pixels aligned in the determined interpolation direction, thereby generating a color image signal including signals of at least two color components. The interpolation processing unit 412 includes a G interpolation color difference calculating unit 412a, a color difference interpolating unit 412b, a color image signal generating unit 412c, a G signal specific frequency component extracting unit 412d, and a specific frequency component addition unit 412e.

With respect to the image signal input from the preprocessing unit 411, the G interpolation color difference calculating unit 412a generates, for a pixel lacking a G signal (R pixel or B pixel), a G signal (hereinafter referred to as an interpolated G signal) interpolated based on surround pixels thereof and outputs a G signal image where all pixel positions have one of a G signal and an interpolated G signal. That is, the interpolation processing by the G interpolation color difference calculating unit 412a generates image signals that form a piece of image where each of the pixels has a pixel value or an interpolation value of the G component.

The G interpolation color difference calculating unit 412a further generates an R-G signal or a B-G signal, which is a color difference signal of a color difference between a signal of a color component and an interpolated G signal according to a position of an R pixel or a B pixel, to output as a color difference image signal. The G interpolation color difference calculating unit 412a outputs the generated G signal image to the color image signal generating unit 412c and outputs the color difference image signal to the color difference interpolating unit 412b.

The color difference interpolating unit 412b performs, on the color difference image signal input from the G interpolation color difference calculating unit 412a, interpolation of a color difference signal lacking at each of pixel positions and outputs a color difference image signal where all pixel positions have a color difference signal to the color image signal generating unit 412c. That is, the interpolation processing by the color difference interpolating unit 412b generates image signals that form a piece of image where each of the pixels has a value of a color difference signal R-G or B-G.

Figure 8:
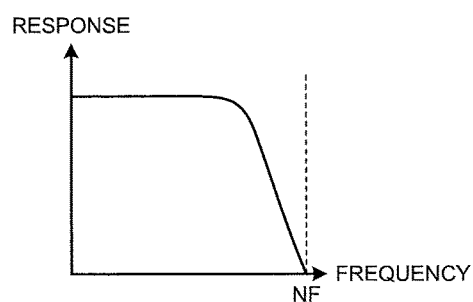
FIG. 8 is a schematic diagram explaining frequency characteristics of interpolation filter processing performed by an interpolation processing unit according to the embodiment of the present invention.

The color image signal generating unit 412c activates an interpolation filter with respect to a G signal, an R-G signal, and a B-G signal generated by the G interpolation color difference calculating unit 412a and the color difference interpolating unit 412b. FIG. 8 is a schematic diagram explaining frequency characteristics of interpolation filter processing performed by the interpolation processing unit 412 according to the embodiment of the present invention. The graph illustrates the signal response relative to the frequency. The color image signal generating unit 412c cuts the Nyquist frequency NF and thus activates an interpolation filter having low-pass filter characteristics as illustrated in FIG. 8 at ½ pixel positions in the horizontal direction and the vertical direction. This interpolation filter processing allows a signal of a pixel position originally included in the image sensor 202 and a signal generated by interpolation processing using a signal value of a surrounding pixel that have frequency characteristics periodically different from each other (especially a G signal has a period of the Nyquist frequency NF) to be spatially uniform.

The color image signal generating unit 412c adds a G signal (including an interpolated G signal) at each of the pixel positions and a color difference signal (B-G signal or R-G signal) after the interpolation filter processing described above to generate an RGB signal or a GB signal and outputs the RGB signal or the GB signal to the display image generation processing unit 413 as a color image signal. Specifically, when an imaging method is WLI, the color image signal generating unit 412c acquires a color difference image signal having a B-G signal and a color difference image signal having an R-G signal from the color difference interpolating unit 412b and generates a signal of an R component, a G component, and a B component (RGB signal). In contrast, when an imaging method is NBI, light of an R component is not present and thus the color image signal generating unit 412c acquires only a color difference image signal having a B-G signal from a B-G interpolation unit 4004 and generates a signal of a G component and a B component (GB signal).

The G signal specific frequency component extracting unit 412d extracts, from signals having red, green, and blue components generated by interpolation, a specific frequency component signal that includes a predetermined spatial frequency component of color signals with respect to a G signal that is a signal of the luminance component in WLI. Specifically, the G signal specific frequency component extracting unit 412d receives a G signal out of the RGB signal generated by the color image signal generating unit 412c and extracts, with respect to the G signal, a specific frequency component signal having a frequency component corresponding to a blood vessel area as a structural object or a dark area (dark part) in a recessed part. A spatial frequency component herein refers to amplitude information of a pixel value for each spatial frequency band obtained by converting a color space forming a predetermined colorimetric system such as R, G, and B into a frequency space.

The specific frequency component addition unit 412e receives an R signal and/or a B signal generated by the color image signal generating unit 412c and the specific frequency component signal extracted by the G signal specific frequency component extracting unit 412d and adds, to the R signal or the B signal, a specific frequency component signal corresponding to a color component thereof. Specifically, the specific frequency component addition unit 412e acquires imaging mode information (information indicating whether an illumination method is the white light imaging (WLI) or the narrow band imaging (NBI)) and adds, to at least one of the R signal and the B signal, a specific frequency component signal corresponding to a color component thereof when the illumination method is WLI. In the case of NBI, a specific frequency component signal corresponding to a B component is added to a B signal.

The display image generation processing unit 413 performs color conversion processing on the color image signal generated by the interpolation processing unit 412 into, for example, a color space of sRGB (XYZ colorimetric system) that is a color gamut of the display unit 5 and further performs tone conversion based on predetermined tone conversion characteristics, enlargement processing, structure enhancing processing of structures such as capillaries or a mucosal fine pattern in the mucosal surface layer, or other processing. After performing predetermined processing, the display image generation processing unit 413 outputs the signal after the processing to the display unit 5 as a display image signal to be displayed.

The input unit 42 is an interface for an operator or others to perform input to the processor 4. The input unit 42 includes: a power switch for turning on/off of power; a mode switching button for switching among a shooting mode and other various modes; and an illumination light switching button for switching illumination light of the light source unit 3.

The storage unit 43 records various programs for operating the endoscope device 1, data including various parameters required for operation of the endoscope device 1, data required for image processing according to an imaging method such as a white balance coefficient, a program to execute the image processing according to the present invention, or other data. The storage unit 43 may further store information related to the endoscope 2, for example a relational table of identification information (ID) of the endoscope 2 and information on filter arrangement of the color filter 202a. The storage unit 43 is implemented by a semiconductor memory such as a flash memory or a dynamic random access memory (DRAM).

The control unit 44 is configured by a CPU or the like. The control unit 44 performs driving control of the respective components including the endoscope 2 and the light source unit 3 as well as input and output control of information with the respective components. The control unit 44 transmits, to the endoscope 2 via a predetermined signal wire, setting data for imaging control (e.g. pixels to be read) recorded in the storage unit 43, a timing signal of an imaging timing, or other data. The control unit 44 outputs color filter information (identification information) acquired via the imaging information storage unit 206 to the image processing unit 41 and outputs information on insertion and removal operation (arrangement) of the switching filter 31c to the light source unit 3.

Next, the display unit 5 will be described. The display unit 5 receives the display image signal generated by the processor 4 via a video cable and displays an in-vivo image corresponding to the display image signal. The display unit 5 is configured by liquid crystal or organic electro luminescence (EL).

Figure 9:
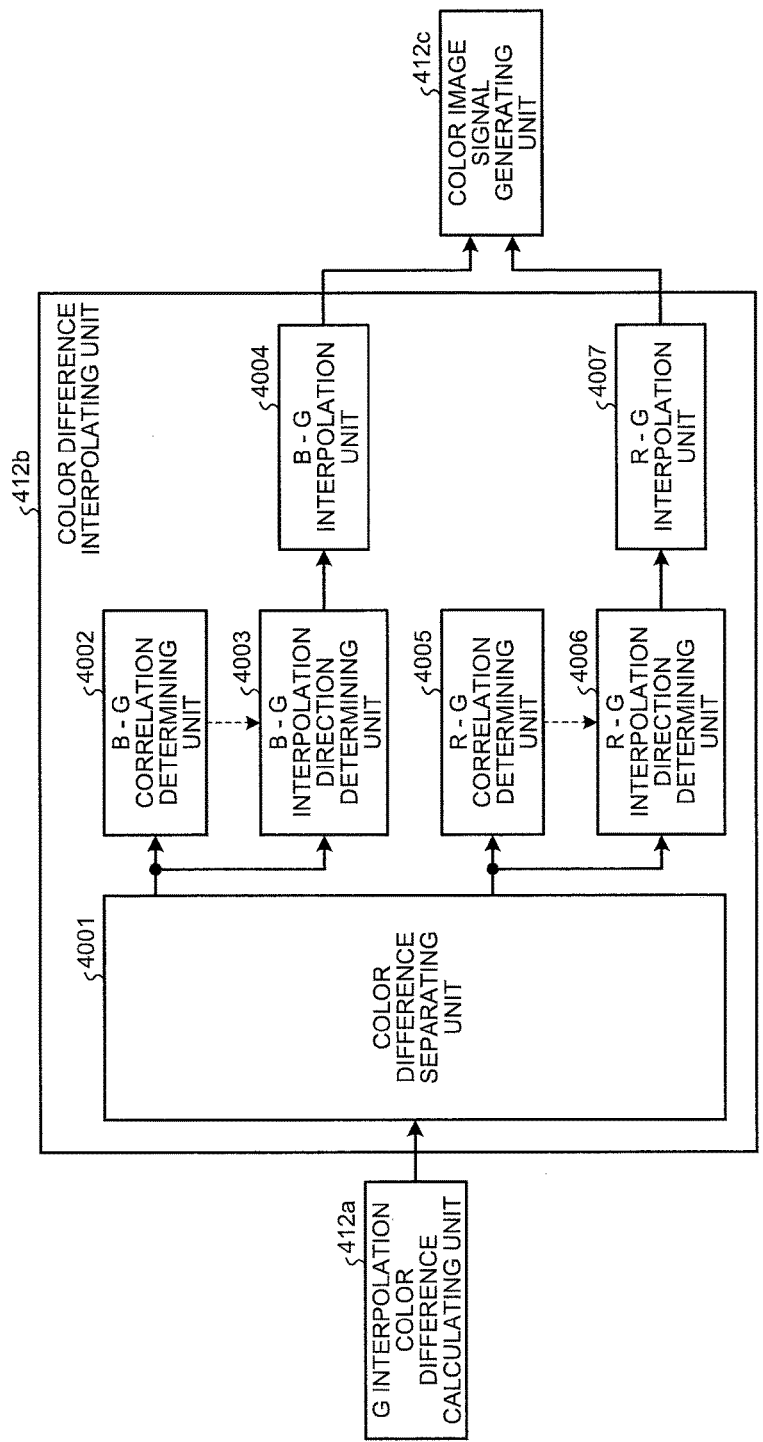
FIG. 9 is a block diagram explaining a configuration of main parts of the interpolation processing unit in the processor according to the embodiment of the present invention.

Subsequently, a configuration of the color difference interpolating unit 412b of the interpolation processing unit 412 will be described with reference to the drawings. FIG. 9 is a block diagram explaining a configuration of main parts of the interpolation processing unit 412. FIG. 9 is a diagram illustrating a configuration of the G interpolation color difference calculating unit 412a, the color difference interpolating unit 412b, and the color image signal generating unit 412c. The color difference interpolating unit 412b includes a color difference separating unit 4001, a B-G correlation determining unit 4002, a B-G interpolation direction determining unit 4003, the B-G interpolation unit 4004, an R-G correlation determining unit 4005, an R-G interpolation direction determining unit 4006, and an R-G interpolation unit 4007.

The color difference separating unit 4001 separates the color difference image signal output from the G interpolation color difference calculating unit 412a into a B-G signal and an R-G signal and outputs the B - G signal to the B-G correlation determining unit 4002 and the B-G interpolation direction determining unit 4003 while outputting the R-G signal to the R-G correlation determining unit 4005 and the R-G interpolation direction determining unit 4006.

FIG. 10 is a schematic diagram explaining demosaicking processing performed by the processor (interpolation processing unit 412). The separated B-G signal and the R-G signal are arranged according to a B pixel position and an R pixel position, respectively, like in the schematic diagram illustrated in FIG. 10.

The B-G correlation determining unit 4002 regards an R pixel having the R-G signal as a pixel of interest with respect to the B-G signal output from the color difference separating unit 4001 and calculates correlation of the B-G signal with a pixel adjacent to the pixel of interest. FIG. 11 is a schematic diagram explaining demosaicking processing performed by the processor (interpolation processing unit 412). Specifically, the B-G correlation determining unit 4002 calculates a correlation value Ss in an obliquely upward direction based on the following formula (1) where a coordinate of a pixel of interest (pixel $P_{ij}$) is (k, l) and a color difference signal value of a B-G signal at four pixel positions adjacent thereto are represented by $f_{B-G}$ (k−1, 1−1), $f_{B-G}$ (k+1, 1−1) $f_{B-G}$ (k−1, 1+1), and $f_{B-G}$ (k+1, 1+1) as illustrated in FIG. 11. Hereinafter an obliquely upward direction refers to a direction from lower left to upper right in the arrangement of pixels illustrated in FIG. 3 and an obliquely downward direction refers to a direction from upper left to lower right in the arrangement of pixels illustrated in FIG. 3 Furthermore, when there is no adjacent pixel such as the case of a pixel positioned at an outer edge, a signal value of a pixel after turning back therefrom is used for example.

$$Ss=|f_{B-G}(k-1, l+1)-f_{B-G}(k+1, l-1)| \qquad (1)$$

The B-G correlation determining unit 4002 further calculates a correlation value Sb in an obliquely downward direction based on the following formula (2).

$$Sb=|f_{B-G}(k-1, l-1)-f_{B-G}(k+1, l+1)| \qquad (2)$$

In the formulas (1) and (2), signal values of two pixels obliquely positioned are used; however, calculation is not limited thereto. Using a B-G signal of a pixel farther in the same direction from a pixel of interest as the center allows for enhancing reliability of a calculated correlation value.

The B-G correlation determining unit 4002 determines that a direction of a smaller one of the correlation values Ss and Sb as a direction with higher correlation when a differential absolute value |Ss−Sb| of the correlation values Ss and Sb is larger than a threshold specified in advance. When the differential absolute value |Ss−Sb| is smaller than a threshold, the B-G correlation determining unit 4002 determines that there is no correlation in a specific direction. The B-G correlation determining unit 4002 outputs evaluation information representing one of "obliquely upward direction", "obliquely downward direction", and "no correlation in a specific direction" to the B-G interpolation direction determining unit 4003. A threshold is set as a value in view of noise included in a signal.

The B-G interpolation direction determining unit 4003 calculates an interpolation color difference signal value $f_{B-G}$ (k, l) of the B-G signal of the pixel of interest (k, l) from one of the following formulas (3) to (5) using the evaluation information from the B-G correlation determining unit 4002 and color difference signal values of B-G signals. When evaluation information is "obliquely upward direction"

The B-G interpolation direction determining unit 4003 calculates an interpolation color difference signal value $f_{B-G}$ (k, l) of the B-G signal of the pixel of interest (k, l) based on the following formula (3) when evaluation information is "obliquely upward direction".

$$f_{B-G}(k, l) = \{f_{B-G}(k-1, l+1) + f_{B-G}(k+1, l-1)\}/2 \quad (3)$$

When evaluation information is "obliquely downward direction"

The B-G interpolation direction determining unit 4003 calculates an interpolation color difference signal value $f_{B-G}$ (k, l) of the B-G signal of the pixel of interest (k, l) based on the following formula (4) when evaluation information is "obliquely downward direction".

$$f_{B-G}(k, l) = \{f_{B-G}(k-1, l+1) + f_{B-G}(k+1, l-1)\}/2 \quad (4)$$

When evaluation information is "no correlation in a specific direction"

The B-G interpolation direction determining unit 4003 calculates an interpolation color difference signal value $f_{B-G}$ (k, l) of the B-G signal of the pixel of interest (k, l) based on the following formula (5) when evaluation information is "no correlation in a specific direction".

$$f_{B-G}(k, l) = \{f_{B-G}(k-1, l+1) + f_{B-G}(k+1, l-1) + f_{B-G}(k-1, l-1) + f_{B-G}(k+1, l+1)\}/4 \quad (5)$$

The formula (5) uses an average value of B-G signals of surrounding four pixels; however, interpolation may be performed using B-G signals of surrounding sixteen or more pixels that can maintain a higher spatial frequency.

The B-G interpolation direction determining unit 4003 calculates the interpolation color difference signal value $f_{B-G}$ (k, l) for the pixel of interest (k, l) and thereby outputs, to the B-G interpolation unit 4004, color difference signals of color difference B-G where B-G signals including interpolated color difference signals are arranged in a checker pattern.

The B-G interpolation unit 4004 calculates an interpolation color difference signal value of a B-G signal for a lacking pixel position with respect to the color difference signals (B-G signals) from the B-G interpolation direction determining unit 4003. The B-G interpolation unit 4004 calculates, for example an interpolation value $f_{B-G}(k, l-1)$ of a missing pixel position (k, l-1) in the arrangement of pixels illustrated in FIG. 11 based on the following formula (6), for example.

$$f_{B-G}(k, l-1) = \{f_{B-G}(k-1, l-1) + f_{B-G}(k, l-2) + f_{B-G}(k+1, l-1) + f_{B-G}(k, l)\}/4 \quad (6)$$

The formula (6) uses an average value of B-G signals of surrounding four pixels; however, interpolation may be performed using B-G signals of surrounding sixteen or more pixels that can maintain a higher spatial frequency.

The B-G interpolation unit 4004 calculates an interpolation color difference signal value for a pixel position where a B-G signal is missing and thereby outputs a color difference image signal where all pixel positions have a B-G signal to the color image signal generating unit 412c. That is, the interpolation processing by the B-G interpolation unit 4004 generates image signals that form a piece of image where each of the pixels has a value of a color difference signal value or an interpolation color difference signal value regarding a color difference B-G.

Similarly to the B-G correlation determining unit 4002, the R-G correlation determining unit 4005 regards a B pixel having the B-G signal as a pixel of interest with respect to the R-G signal output from the color difference separating unit 4001 and calculates correlation of the R-G signal with a pixel adjacent to the pixel of interest. The R-G correlation determining unit 4005 calculates correlation values Ss and Sb while replacing B with R in the formulas (1) and (2). The R-G correlation determining unit 4005 determines one of "obliquely upward direction", "obliquely downward direction", and "no correlation in a specific direction" based on the correlation value Ss, the correlation value Sb, the differential absolute value |Ss−Sb| and the threshold and outputs the evaluation information representing the evaluation result to the R-G interpolation direction determining unit 4006.

Similarly to the B-G interpolation direction determining unit 4003, the R-G interpolation direction determining unit 4006 calculates an interpolation color difference signal value $f_{R-G}$ (k, l) of the R-G signal for the pixel of interest (k, l) from one of the above formulas (3) to (5) using the evaluation information from the R-G correlation determining unit 4005 and color difference signal values of R-G signals. The R-G interpolation direction determining unit 4006 calculates an interpolation color difference signal value $f_{R-G}$ (k, l) while replacing B with R in the formulas (3) to (5). The R-G interpolation direction determining unit 4006 calculates the interpolation color difference signal value $f_{R-G}$ (k, l) for the pixel of interest (k, l) and thereby outputs, to the R-G interpolation unit 4007, color difference signals of color difference R-G where R-G signals including interpolated color difference signals are arranged in a checker pattern.

Similarly to the B-G interpolation unit 4004, the R-G interpolation unit 4007 calculates an interpolation color difference signal value of an R-G signal for a lacking pixel position with respect to the color difference signals (R-G signals) from the R-G interpolation direction determining unit 4006. The R-G interpolation unit 4007 calculates an interpolation color difference signal value for a pixel position lacking an R-G signal and thereby outputs a color difference image signal where all pixel positions have an R-G signal to the color image signal generating unit 412c. That is, the interpolation processing by the R-G interpolation unit 4007 generates image signals that form a piece of image where each of the pixels has a value of a color difference signal value or an interpolation color difference signal value regarding a color difference R-G.

The color difference interpolating unit 412b outputs the color difference signal to the color image signal generating unit 412c by the interpolation processing described above. When an imaging method is WLI, the B-G interpolation unit 4004 and the R-G interpolation unit 4007 output a color difference image signal having the B-G signal and a color difference image signal having the R-G signal, respectively. In contrast, when an imaging method is NBI, light of the R component is not present and thus the color image signal generating unit 412c receives only the color difference image signal having the B-G signal from the B-G interpolation unit 4004.

Figure 12:
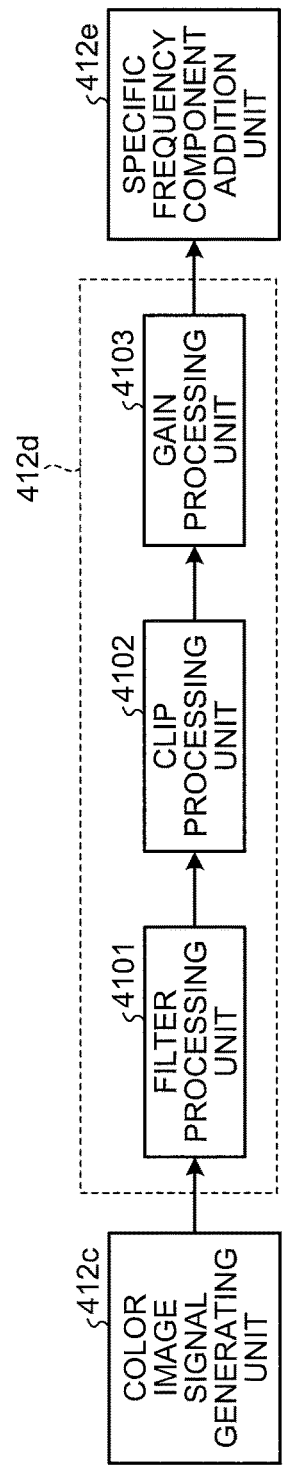
FIG. 12 is a block diagram explaining a configuration of main parts of the interpolation processing unit of the processor according to the embodiment of the present invention.

Next, a configuration of the G signal specific frequency component extracting unit 412d of the interpolation processing unit 412 will be described with reference to the drawings. FIG. 12 is a block diagram explaining a configuration of main parts of the interpolation processing unit 412. FIG. 12 is a diagram illustrating a configuration of the color image signal generating unit 412c, the G signal specific frequency component extracting unit 412d, and the specific frequency component addition unit 412e. The G signal specific frequency component extracting unit 412d includes a filter processing unit 4101, a clip processing unit 4102, and a gain processing unit 4103.

Figure 13:
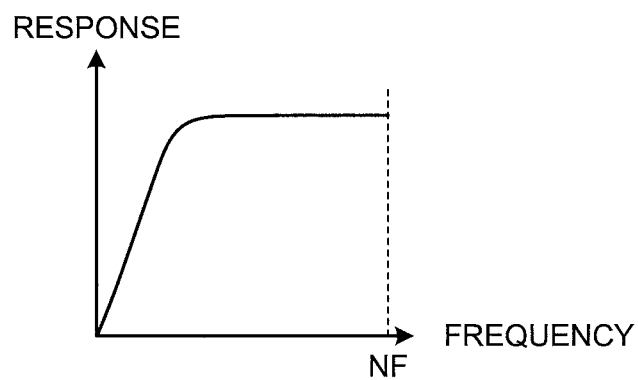
FIG. 13 is a schematic diagram explaining frequency characteristics of filtering processing performed by a filter processing unit according to the embodiment of the present invention.
Figure 14:
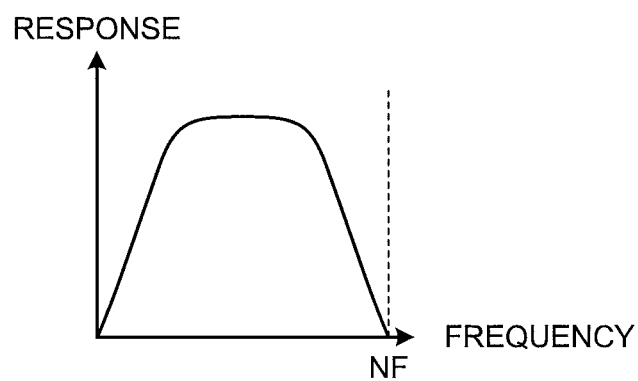
FIG. 14 is a schematic diagram explaining frequency characteristics of the filtering processing performed by the filter processing unit according to the embodiment of the present invention.
Figure 15:
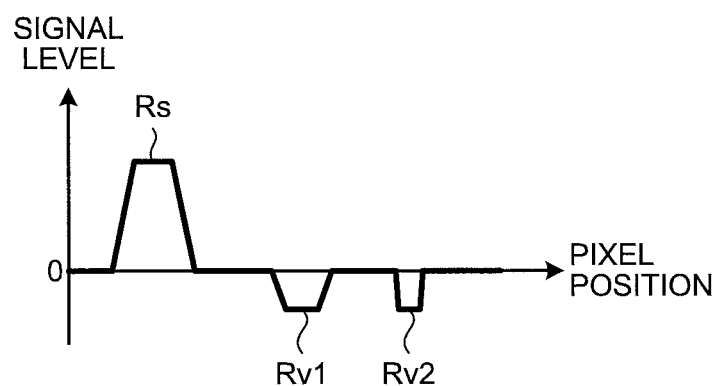
FIG. 15 is a schematic diagram explaining a signal after the filtering processing performed by the filter processing unit according to the embodiment of the present invention.

The filter processing unit 4101 receives a G signal out of the RGB signal generated by the color image signal generating unit 412c and performs filter processing by a high-pass filter. FIGS. 13 and 14 are schematic diagrams for explaining frequency characteristics of the filtering processing performed by the filter processing unit 4101 according to the embodiment of the present invention. FIG. 15 is a schematic diagram explaining a signal after the filtering processing performed by the filter processing unit 4101 according to the embodiment of the present invention. FIG. 15 illustrates a signal level at pixel positions in one line (e.g. horizontal direction) of the pixel array illustrated in FIG. 3. A G signal here is limited to having the frequency characteristics as illustrated in FIG. 8 by the interpolation filter processing in the color image signal generating unit 412c. The filter processing unit 4101 performs filter processing on the G signal generated by the color image signal generating unit 412c by a high-pass filter having response characteristics (frequency characteristics) as illustrated in FIG. 13.

The G signal subjected to high-pass filter processing by the filter processing unit 4101 has synthesized characteristics of the frequency characteristics illustrated in FIG. 8 and the frequency characteristics illustrated in FIG. 13. As a result, the G signal becomes a signal (response signal) having band-pass characteristics limited to the frequency characteristics illustrated in FIG. 14. As a result of this, a signal having band-pass characteristics output from the filter processing unit 4101 becomes a specific frequency component signal having positive and negative values with a level zero as a reference where a low frequency component is cut off as illustrated in FIG. 15. Specifically, an area $R_s$ of a positive value corresponds to a bright small area such as a small bright spot, a bright area of a protruding part of a living body, a mucosal area where the hemoglobin content is locally smaller than that in a surrounding area, or other areas while areas $R_v1$ and $R_v2$ of a negative value correspond to blood vessels or a dark area of a recessed part.

The blood vessels in the mucosa absorbs light of the narrow band $T_G$ due to hemoglobin contained in the blood. Thus blood vessels of small diameters in the mucosal surface layer, blood vessels of medium diameters in the mucosal middle layer, and blood vessels of large diameters in the mucosal deep layer form dark areas with less reflection light. The amount of absorption of light of the narrow band $T_G$ increases as the amount of hemoglobin increases (that is, as thicker the blood vessels are). Areas other than the blood vessel contains less hemoglobin and thus have more reflection light as compared to areas of blood vessels, thereby forming bright areas (with a high luminance value) on average. The level zero illustrated in FIG. 15 generally corresponds to a signal level of an area other than that of the blood vessels. Especially, characteristics of a high-pass filter is designed such that the blood vessels of large diameters that are blood vessels in the deep layer are mostly cut due to the high-pass filter characteristics processed by the filter processing unit 4101 and that blood vessels in the middle and the surface layers are extracted. Frequency characteristics of the blood vessels in a G signal varies depending on an observation distance and the number of pixels of the endoscope 2 (insertion unit 21). Determining the high-pass filter characteristics based on a predetermined observation distance and the number of pixels allows for maintaining a state where the blood vessels of large diameters are cut from a specific frequency component signal upon approaching closer than the predetermined observation distance. Especially in NBI, it is possible to set the predetermined observation distance since in a distant vision observation of colors in a wider area (area appearing in dark reddish brown where the surface layer blood vessels are dense) is mainly performed while in a proximity state diagnosis is made with the main focus on evaluating a running state of the surface layer blood vessels.

Figure 16:
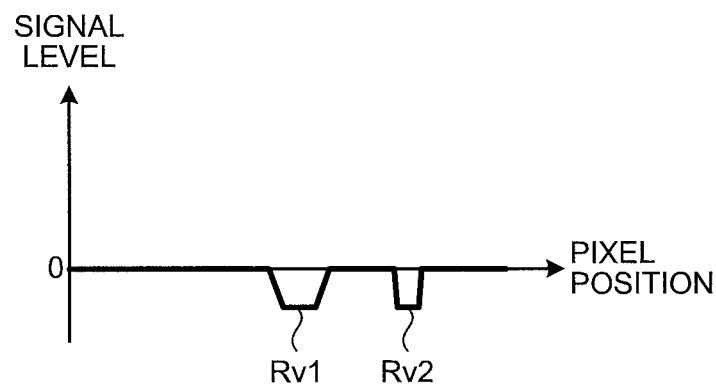
FIG. 16 is a schematic diagram explaining signals after clip processing performed by a clip processing unit according to the embodiment of the present invention.

The clip processing unit 4102 receives the specific frequency component signal output from the filter processing unit 4101 as illustrated in FIG. 15 and generates a specific frequency component signal limited by clip thresholds different between a positive value and a negative value that are set in advance. FIG. 16 is a schematic diagram explaining a signal after clip processing by the clip processing unit 4102 according to the embodiment of the present invention. The clip processing unit 4102 extracts levels based on a range (clip range) set by a clip upper limit value of the level zero and a clip lower limit value of a predetermined negative value. An absolute value of the clip lower limit value in the embodiment is larger than an absolute value of the areas $R_v1$ and $R_v2$ described above. The clip processing unit 4102 cuts the area $R_s$ of a bright spot or other areas while extracting only the areas $R_v1$ and $R_v2$ of a blood vessel area or a dark area of a recessed part. The specific frequency component signal subjected to clip processing by the clip processing unit 4102 is output to the gain processing unit 4103. In the clip processing described above, the clip processing unit 4102 extracts blood vessels areas by the two thresholds; however, extraction is not limited thereto. A clip upper limit value may be a predetermined positive value to allow for extracting a change in the mucosal surface layer. Alternatively, combining nonlinear low-pass processing such as morphology allows for extracting only a recessed part of a predetermined width or less. The clip range described above may be the same range regardless of an imaging method or may be different ranges depending on an imaging method. In this case, the clip processing unit 4102 acquires the imaging mode information from the control unit 44, determines an imaging method, and performs signal extraction within a clip range according to the determined imaging method.

Figure 17:
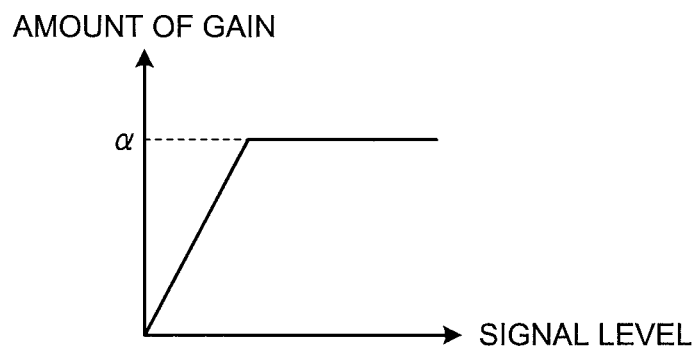
FIG. 17 is a schematic diagram explaining gain processing performed by a gain processing unit according to the embodiment of the present invention.

The gain processing unit 4103 calculates the amount of gain with respect to a signal value of the G signal after the clip processing by the clip processing unit 4102 and multiplies the specific frequency component signal with the calculated the amount of gain. FIG. 17 is a schematic diagram explaining gain processing performed by the gain processing unit 4103 according to the embodiment of the present invention. Specifically, the gain processing unit 4103 receives the specific frequency component signal after the clip processing output from the clip processing unit 4102 and the G signal output from the color image signal generating unit 412c. The gain processing unit 4103 calculates the amount of gain corresponding to a level of a G signal as illustrated in FIG. 17, multiplies the specific frequency component signal with the calculated the amount of gain, and outputs the obtained final specific frequency component signal to the specific frequency component addition unit 412e. The reason for assuming the amount of gain having characteristics as illustrated in FIG. 17 is because an object is to suppress an increase in the amount of noise in a dark part and to thereby amplify amplitude of a blood vessel area extracted in an area having predetermined brightness or more by α times. The value α is determined in advance as an amount that complements attenuation of the blood vessels drawn by a B signal or an R signal due to the preceding interpolation processing.

Figure 18:
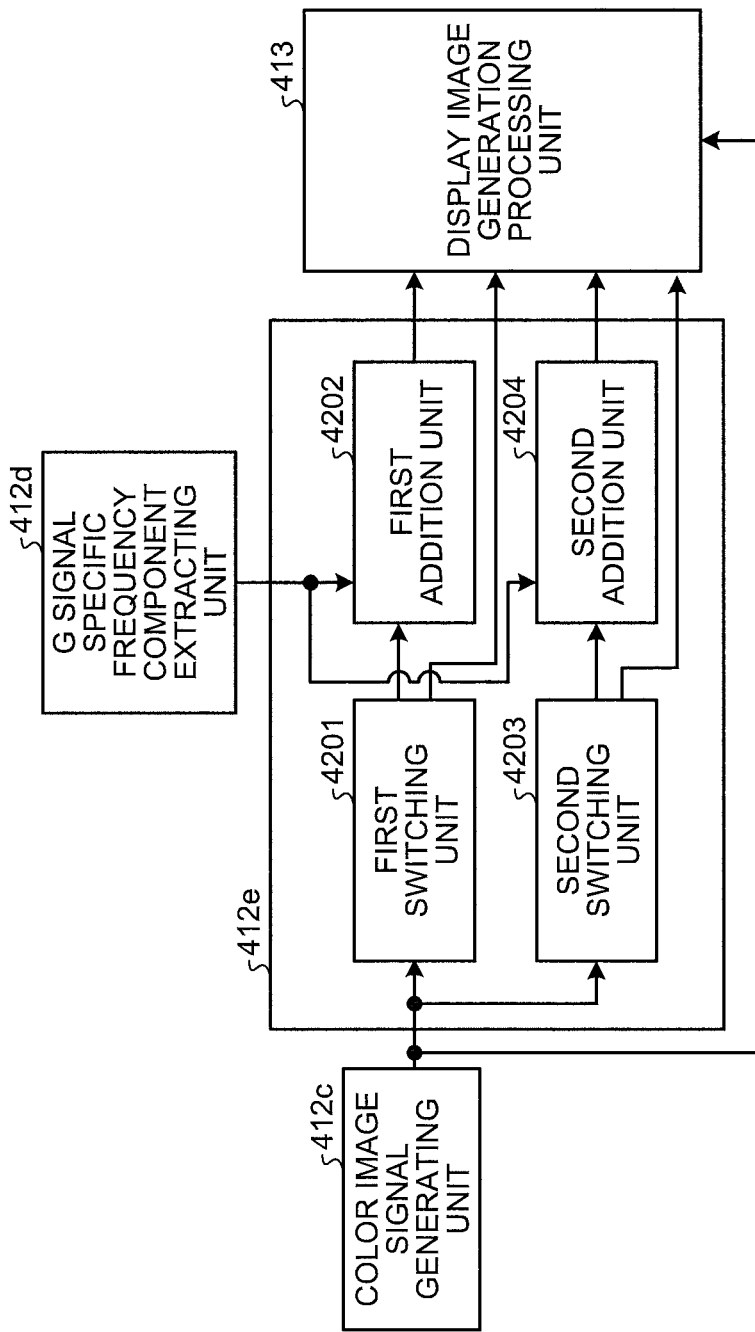
FIG. 18 is a block diagram explaining a configuration of main parts of the interpolation processing unit of the processor according to the embodiment of the present invention.

Next, a configuration of the specific frequency component addition unit 412e of the interpolation processing unit 412 will be described with reference to the drawings. FIG. 18 is a block diagram explaining a configuration of main parts of the interpolation processing unit 412. FIG. 18 is a diagram illustrating a configuration of the color image signal generating unit 412c, the G signal specific frequency component extracting unit 412d, the specific frequency component addition unit 412e, and the display image generation processing unit 413. The specific frequency component addition unit 412e includes a first switching unit 4201, a first addition unit 4202, a second switching unit 4203, and a second addition unit 4204.

The first switching unit 4201 receives a B signal from the color image signal generating unit 412c and outputs the input B signal to the display image generation processing unit 413 when acquiring imaging mode information showing that an illumination method is WLI. On the contrary, when acquiring imaging mode information showing that an illumination method is NBI, the first switching unit 4201 outputs the input B signal to the first addition unit 4202. In this manner, the first switching unit 4201 switches a destination of the input B signal depending on the imaging mode information (illumination method).

The first addition unit 4202 receives the B signal output from the first switching unit 4201 and the specific frequency component signal output from the G signal specific frequency component extracting unit 412d and adds the specific frequency component signal to the B signal. The first addition unit 4202 outputs the added B signal obtained by the addition to the display image generation processing unit 413.

The second switching unit 4203 receives an R signal from the color image signal generating unit 412c and outputs the input R signal to the display image generation processing unit 413 when acquiring imaging mode information showing that an illumination method is NBI. On the contrary, when acquiring imaging mode information showing that an illumination method is WLI, the second switching unit 4203 outputs the input R signal to the second addition unit 4204. In this manner, the second switching unit 4203 switches a destination of the input R signal depending on the imaging mode information (illumination method).

The second addition unit 4204 receives the R signal output from the second switching unit 4203 and the specific frequency component signal output from the G signal specific frequency component extracting unit 412d, and adds the specific frequency component signal to the R signal. The second addition unit 4204 outputs the added R signal obtained by the addition to the display image generation processing unit 413.

Here, reference will be made to the reason for adding the specific frequency component signal to the B signal when the illumination method is NBI. Since the surface layer blood vessels include less hemoglobin and thus absorb less light of the narrow band $T_G$. Therefore, a difference in a signal value with the surrounding mucosa is small. The blood vessels of medium diameters include more hemoglobin than the surface layer blood vessels and thus absorb more light of the narrow band $T_G$. Therefore, a difference in a signal value with the surrounding mucosa can be obtained.

The interpolation processing is performed on the B signal to maintain a frequency band as much as possible by the color difference interpolating unit 412b and the color image signal generating unit 412c as described above; however, the interpolation processing itself has low-pass filter characteristics and thus a high frequency component is attenuated, resulting in an image where a contrast (signal amplitude) of images of the blood vessels of small diameters or the blood vessels of medium diameters is reduced.

From the specific frequency component signal extracted from the G signal, no signal corresponding to an image of the blood vessels of large diameters is not extracted but a signal corresponding to an image of the blood vessels of medium diameters and the blood vessels of small diameters is extracted as the specific frequency component signal. The clip processing does not extract an area other than that of the blood vessels while suppressing noise unnecessary for the specific frequency component signal from being mixed.

Adding such a specific frequency component signal to a B signal allows for adding an image of the specific frequency component signal of the blood vessels of small diameters or the blood vessels of medium diameters to an image of the blood vessels of small diameters or the blood vessels of medium diameters of the B signal, respectively, thereby enhancing a contrast of the image of the blood vessels of the B signal as compared to the case of using only the B signal.

Furthermore, when an illumination method is NBI, there are cases where the capillaries in the shallow mucosal surface layer absorb only light of the narrow band $T_B$ and thus light of the narrow band $T_G$ is hardly absorbed. In such case, an image of the capillaries cannot be drawn by a G signal and a specific frequency component of the G signal cannot be added to the G signal. In this case, performing direction determining interpolation on a B-G signal by the color difference interpolating unit 412b allows for suppressing deterioration of resolution of the B signal to the minimum.

The display image generation processing unit 413 performs the aforementioned processing on the G signal output from the color image signal generating unit 412c and the B signal (or the added B signal) and the R signal (or the added R signal) output from the specific frequency component addition unit 412e and then outputs the processed signal to the display unit 5 as a display image signal to be displayed.

Figure 19:
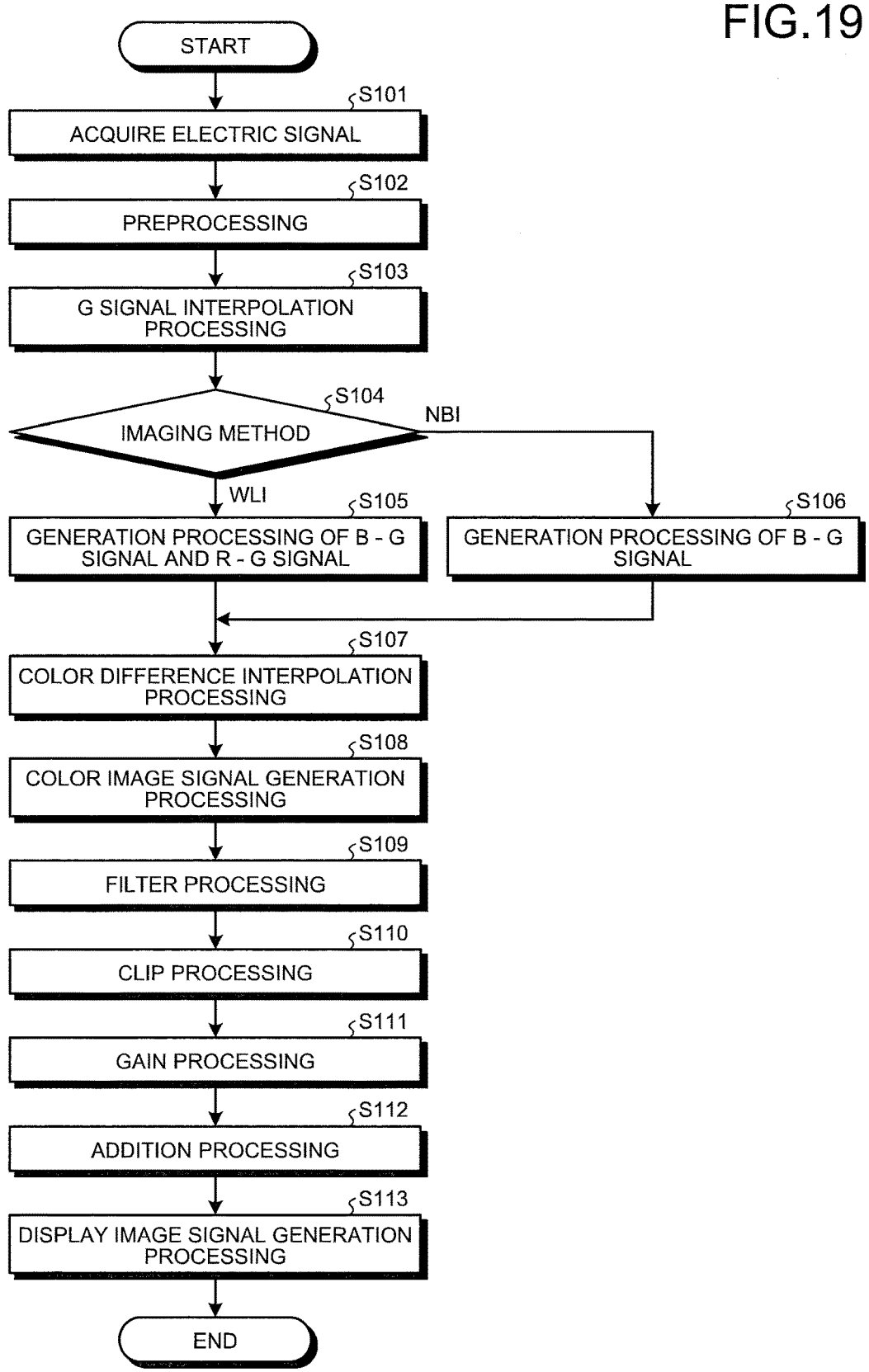
FIG. 19 is a flowchart for explaining signal processing performed by the processor according to the embodiment of the present invention.

Subsequently, signal processing (image processing method) performed by the processor 4 will be described with reference to the drawings. FIG. 19 is a flowchart for explaining signal processing performed by the processor 4. The processor 4 acquires an electric signal from the endoscope 2 (distal end part 24) and then outputs the electric signal to the preprocessing unit 411 (step S101). The electric signal from the endoscope 2 is generated by the image sensor 202 and includes RAW image data converted into a digital signal by the A/D converter 205.

When the electric signal is input to the preprocessing unit 411, the preprocessing unit 411 performs the OB clamp processing, the noise reduction processing, and the white balance processing described above and then outputs an image signal after the signal processing to the interpolation processing unit 412 (step S102).

When the electric signal applied with the signal processing by the preprocessing unit 411 is input to the interpolation processing unit 412, the G interpolation color difference calculating unit 412a generates, for a pixel lacking a G signal (R pixel or B pixel), an interpolated G signal and outputs a G signal image where all pixel positions have one of a G signal (pixel value) and an interpolated G signal (interpolated value) to the color image signal generating unit 412c (step S103).

Thereafter the G interpolation color difference calculating unit 412a acquires imaging mode information and determines imaging method (illumination method) by which the input electric signal has been generated, among the white light imaging and the narrow band imaging (step S104). Specifically, the G interpolation color difference calculating unit 412a determines by which imaging method the electric signal has been generated based on a control signal from the control unit 44 (e.g. information on illumination light or information representing an imaging method).

When determining that the input electric signal has been generated by the white light imaging (WLI in step S104), the G interpolation color difference calculating unit 412a generates an R-G signal and a B-G signal that are color difference signals of color differences between a signal of each of color components and an interpolated G signal corresponding to a position of an R pixel and a B pixel, respectively, and outputs the signals to the color difference interpolating unit 412b as color difference image signals (step S105).

Contrary to this, when determining that the input electric signal has been generated by the narrow band imaging (NBI in step S104), the G interpolation color difference calculating unit 412a generates a B-G signal that is a color difference signal of a color difference between a signal of a B component and an interpolated G signal corresponding to a position of a B pixel, and outputs the signal to the color difference interpolating unit 412b as a color difference image signal (step S106).

The color difference interpolating unit 412b performs color difference interpolation processing based on the color difference image signal acquired from the G interpolation color difference calculating unit 412a (step S107). Specifically, the color difference interpolating unit 412b performs, on the color difference image signal input from the G interpolation color difference calculating unit 412a, interpolation of a color difference signal lacking at each of pixel positions and outputs a color difference image signal where all pixel positions have a color difference signal to the color image signal generating unit 412c. That is, image signals that form one piece of image where each pixel has a value of color difference signals R-G and B-G are generated by the interpolation processing by the color difference interpolating unit 412b in the case of the white light imaging. In the case of the narrow band imaging, image signals that form one piece of image where each pixel has a value of a color difference signal B-G are generated.

The color image signal generating unit 412c generates a color image signal that forms a color image using a pixel value and an interpolated value of a G component generated by the G interpolation color difference calculating unit 412a as well as a signal value of the color difference image signal generated by the color difference interpolating unit 412b (step S108). Specifically, the color image signal generating unit 412c adds a G signal or an interpolated G signal at each pixel position and a color difference signal (B-G signal or R-G signal) to generate an RGB signal or a GB signal and outputs the G signal to the G signal specific frequency component extracting unit 412d and the display image generation processing unit 413 while outputting an RB signal to the specific frequency component addition unit 412e.

Thereafter, the G signal specific frequency component extracting unit 412d extracts a specific frequency component signal for the G signal out of the RGB signal generated by the color image signal generating unit 412c. Specifically, the filter processing unit 4101 receives the G signal out of the RGB signal generated by the color image signal generating unit 412c and performs filter processing by a high-pass filter (step S109).

The clip processing unit 4102 performs clip processing on the specific frequency component signal output from the filter processing unit 4101 (see FIG. 15) and generates a specific frequency component signal limited by a clip lower limit value and a clip upper limit value set in advance (step S110, specific frequency component extracting step).

The gain processing unit 4103 calculates the amount of gain with respect to a signal value of the G signal after the clip processing by the clip processing unit 4102 and multiplies the specific frequency component signal with the calculated the amount of gain (step S111).

Then the specific frequency component addition unit 412e receives the R signal and the B signal generated by the color image signal generating unit 412c and the specific frequency component signal extracted by the G signal specific frequency component extracting unit 412d and adds, to the R signal and the B signal, a specific frequency component signal corresponding to a color component thereof according to the imaging mode information (step S112, specific frequency component adding step). The specific frequency component addition unit 412e refers to the imaging mode information described above and adds to the R signal and the B signal a specific frequency component signal corresponding to a color component thereof when the illumination method is WLI. In the case of NBI, a specific frequency component signal corresponding to a B component is added to the B signal.

The display image generation processing unit 413 performs tone conversion, enlargement processing, structure enhancing processing of structures such as capillaries or a mucosal fine pattern in the mucosal surface layer, or other processing on the G signal output from the color image signal generating unit 412c and the B signal (or an added B signal) and the R signal (or an added R signal) output from the specific frequency component addition unit 412e and thereby generates a display image signal to be displayed (step S113). After performing predetermined processing, the display image generation processing unit 413 outputs the signal to the display unit 5 as a display image signal.

According to the embodiment described above, in the endoscope device capable of switching between WLI and NBI, the G signal specific frequency component extracting unit 412d extracts a specific frequency component signal from a G signal out of an RGB signal generated by the color image signal generating unit 412c for a color image signal generated by the color image signal generating unit 412c and the specific frequency component addition unit 412e adds the specific frequency component signal to a B signal. Therefore, deterioration of a contrast in blood vessels due to interpolation processing can be suppressed. In the embodiment, a high resolution is ensured by performing interpolation processing using a signal value of a G pixel in the case of WLI while, in the case of NBI, a specific frequency component signal is added to a signal of a blue component to complement an area corresponding to blood vessels or a dark area of a recessed part and thus a resolution of a luminance component can be enhanced in any of the white light imaging where a green component is the luminance component and the narrow band imaging where a blue component is the luminance component.

Moreover, according to the embodiment described above, a direction with higher correlation is determined for a B-G signal or an R-G signal using only a B-G signal or an R-G signal surrounding a position of the pixel of interest and interpolation is performed using a B-G signal or an R-G signal in the determined direction with high correlation. Therefore, deterioration of a resolution of structural objects such as capillaries or blood vessels in the deep layer that are hardly correlated with a G signal can be suppressed to the minimum.

Modification of Embodiments

Figure 20:
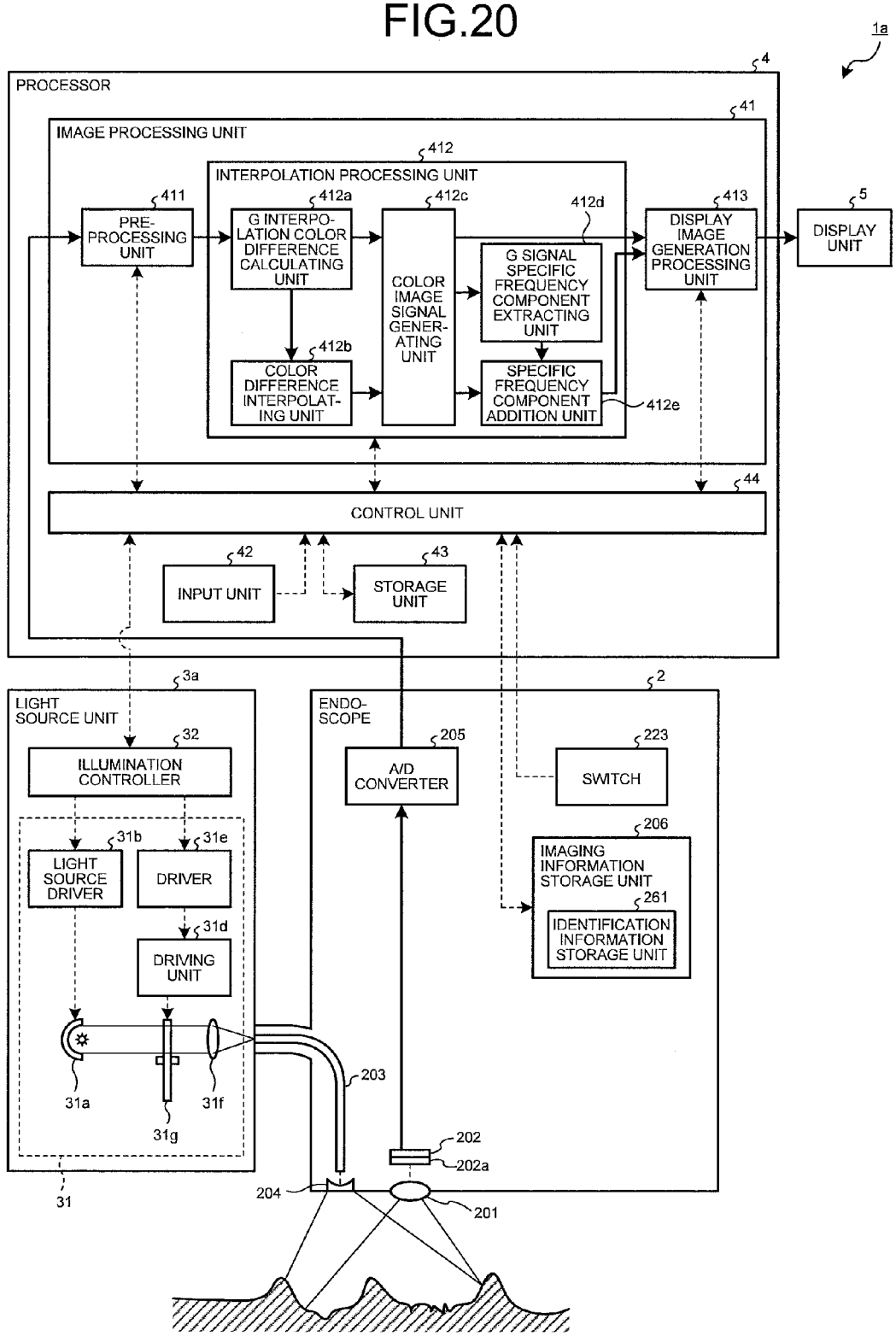
FIG. 20 is a schematic diagram illustrating a schematic configuration of an endoscope device according to a modification of the embodiment of the present invention.

FIG. 20 is a schematic diagram illustrating a schematic configuration of an endoscope device 1a according to a modification of the embodiment of the present invention. In the embodiment described above, the light source unit 3 includes the switching filter 31c and an imaging method is switched by inserting or removing the switching filter 31c to one of the white light imaging and the narrow band imaging using the narrow band illumination light formed by light of the narrow bands $T_B$ and $T_G$; however, in the modification, a light source unit 3a is provided instead of the light source unit 3 and the imaging method is switched by a rotation filter 31g.

The endoscope device 1a according to the modification includes the endoscope 2, the processor 4, and the display unit 5 that are described above as well as a light source unit 3a that generates illumination light to be emitted from a distal end of the endoscope 2. The light source unit 3a includes an illumination unit 31 and an illumination controller 32. The illumination unit 31 switches between a plurality of rays of illumination light having different wavelength bands, and emits the illumination light under control by the illumination controller 32. The illumination unit 31 includes the light source 31a described above, a light source driver 31b, a driving unit 31d, a driver 31e, a condenser lens 31f, and a rotation filter 31g.

Figure 21:
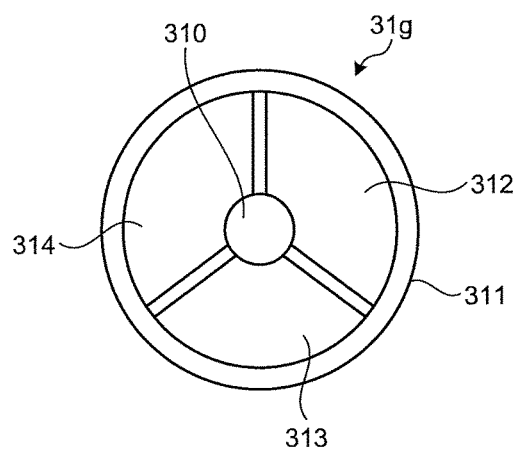
FIG. 21 is a schematic diagram illustrating a configuration of a rotation filter of a light source unit according to the modification of the embodiment of the present invention.

FIG. 21 is a schematic diagram illustrating a configuration of the rotation filter 31g of the light source unit 3a according to the modification of the embodiment of the present invention. The rotation filter 31g includes a rotation shaft 310 and a rotation part 311 of a disk shape supported by the rotation shaft 310. The rotation part 311 includes three filters (filters 312 to 314) arranged at each of three areas divided from the principal surface thereof.

The filter 312 passes white illumination light including light of the red, the green, and the blue wavelength bands $H_R$, $H_G$, $H_B$.

The filter 313 passes narrow band illumination light (referred to as first narrow band illumination light in the modification) formed by light of a narrow band $T_B$ (e.g. 400 nm to 445 nm) included in the wavelength band $H_B$ and light of a narrow band $T_G$ (e.g. 530 nm to 550 nm) included in the wavelength band $H_G$. Light passed through by the filter 313 corresponds to the narrow band illumination light of the narrow band imaging (NBI) described above.

Figure 22:
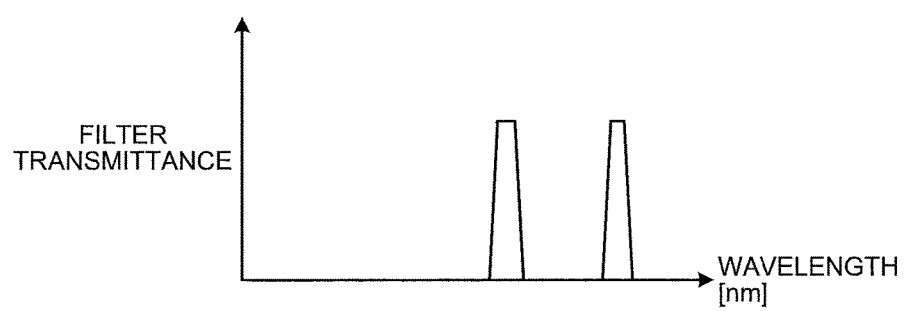
FIG. 22 is a graph illustrating relationship between the wavelength and the transmittance of illumination light through a filter included in an illumination unit of the endoscope device according to the modification of the embodiment of the present invention.

FIG. 22 is a graph illustrating relationship between the wavelength and the transmittance of illumination light through a filter included in the illumination unit 31 of the endoscope device 1a according to the modification of the embodiment of the present invention. The filter 314 passes narrow band illumination light (referred to as second narrow band illumination light in the modification) formed by light of a narrow band $T_R$ included in the wavelength band $H_R$ and light of a narrow band $T_G$ included in the wavelength band $H_G$. Light of the narrow band $T_G$ passed through the filter 314 may be the same as light of the narrow band $T_G$ of the narrow band imaging (NBI) described above or may be of a different band. Under the second narrow band illumination light, for example a color component having a large variation is selected as a luminance component out of a red component (narrow band $T_R$) and a green component (narrow band $T_G$).

The illumination controller 32 controls the light source driver 31b to cause on/off operation of the light source 31a and controls the driver 31e to rotate the rotation filter 31g (rotation shaft 310) to thereby dispose one of the filters 312 to 314 on an optical path of the light source 31a, thereby controlling the type (band) of illumination light emitted by the illumination unit 31.

Also in the modification, an image processing unit 41 performs the signal processing described above to generate a display image signal. Light of a B component is not present in the case of imaging by the second narrow band illumination light and thus a color image signal generating unit 412c receives only a color difference image signal having an R-G signal from an R-G interpolation unit 4007. The color image signal generating unit 412c then generates a signal of an R component and a G component (RG signal).

The filter processing unit 4101 receives a G signal out of the RGB signal generated by the color image signal generating unit 412c and performs filter processing by a predetermined high-pass filter. In the modification, a filter processing unit 4101 may extract a signal having band-pass characteristics different for each imaging method. Specifically, the filter processing unit 4101 may extract a signal having band-pass characteristics limited to the frequency characteristics illustrated in FIG. 14 when the imaging method is NBI while extracting a signal having frequency characteristics of a predetermined range by predetermined band-pass filter processing in the case of the imaging method using the second narrow band illumination light. Cutting a high frequency by a band-pass filter instead of a high-pass filter in the case of the imaging method using the second narrow band illumination light allows for excluding the blood vessels of small diameters in the mucosal surface layer that are unnecessary for imaging by the second narrow band illumination light.

A clip processing unit 4102 switches a threshold (range of signal amplitude) for clip processing according to imaging mode information (imaging method). The threshold for each of the imaging methods may be stored in a storage unit 43 in advance and be referred to therefrom or may be input via an input unit 42 by an operator or others for performance of clip processing.

A first switching unit 4201 receives a B signal from a color image signal generating unit 412c and outputs the input B signal to a display image generation processing unit 413 when acquiring imaging mode information showing that the illumination method is WLI or the method using the second narrow band illumination light. On the contrary, when acquiring imaging mode information showing that an illumination method is NBI, the first switching unit 4201 outputs the input B signal to a first addition unit 4202.

A second switching unit 4203 receives an R signal from the color image signal generating unit 412c and outputs the input R signal to the display image generation processing unit 413 when acquiring imaging mode information showing that an illumination method is NBI. On the contrary, when acquiring imaging mode information showing that an illumination method is WLI or a method using the second narrow band illumination light, the second switching unit 4203 outputs the input R signal to a second addition unit 4204.

In the embodiment described above, the color filter 202a including the plurality of filters each passing light of a predetermined wavelength band is provided on the light-receiving surface of the image sensor 202; however, each of the filters may be separately provided to each pixel of the image sensor 202.

The endoscope devices 1 and 1a according to the embodiment described above switch illumination light emitted from the illumination unit 31 to one of the white illumination light and the narrow band illumination light by inserting or removing the switching filter 31c or by rotating the rotation filter 31g with respect to white light emitted from one light source 31a; however, switching between two light sources for emitting white illumination light and narrow band illumination light, respectively, may be employed to emit one of the white illumination light and the narrow band illumination light. As a device for emitting one of the white illumination light and the narrow band illumination light by switching between the two light sources, a capsule endoscope may be employed which includes the light sources, a color filter, and an image sensor and which is configured to be introduced into a subject, for example.

The endoscope devices 1 and 1a according to the embodiment and the modification described above include the A/D converter 205 at the distal end part 24; however, the A/D converter 205 may be included in the processor 4. Furthermore, the configuration related to the image processing may be included in the endoscope 2, a connector connecting the endoscope 2 and the processor 4, or the operating unit 22. The endoscope devices 1 and 1a described above identify the endoscope 2 connected to the processor 4 using the identification information or other information stored in the imaging information storage unit 206; however, an identification unit may be provided to a connection part (connector) between the processor 4 and the endoscope 2. For example, a pin for identification (identification unit) may be included on the endoscope 2 side to identify the endoscope 2 connected to the processor 4.

In the embodiment described above, the G interpolation color difference calculating unit 412a generates a G signal interpolated based on surrounding pixels for a pixel lacking a G signal (R pixel or B pixel); however, linear interpolation to perform interpolation processing by determining an interpolation direction may be employed. Alternatively, interpolation processing may be performed by cubic interpolation or other non-linear interpolation.

In the embodiment described above, the second switching unit 4203 outputs the input R signal to the second addition unit 4204 when acquiring imaging mode information showing that the illumination method is WLI; however, the input R signal may be output to the display image generation processing unit 413. That is, the adding processing of the specific frequency component signal may not be performed in WLI. Causing the specific frequency component not to be added in WLI allows for suppressing a change in colors of the blood vessels.

In the embodiment described above, the clip processing by the clip processing unit 4102 may not be performed while a response signal extracted by the filter processing unit 4101 may be output to the gain processing unit 4103 as the specific frequency component signal.

In the embodiment described above, the filter units U1 of a Bayer array are arranged in a matrix in the color filter 202a; however, the filter unit U1 is not limited to a Bayer array. For example, in switching between WLI and NBI, a filter unit is only required to have a filter array having a higher density of G component than that of a B component. Any filter array may be employed as long as the filter array has a higher density of pixels that generate an electric signal of a luminance component of white illumination light than a density of pixels that generate an electric signal of a luminance component of narrow band illumination light.

The exemplary endoscope device including the image processing apparatus has been employed in the above embodiments; however, an imaging device for performing image processing, such as a microscopic device, may also be employed in some embodiments.

According to some embodiments, it is possible to acquire high resolution images in any of the white light imaging and the narrow band imaging.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus for interpolating a signal of a missing color component based on first, second, and third color signals respectively generated by first, second, and third pixels of an image sensor, to generate an image signal having color signals of color components, the first, second, and third pixels being arranged in a matrix, the first pixels being configured to generate the first color signal of a first luminance component that is a luminance component of white illumination light including red wavelength band light, green wavelength band light, and blue wavelength band light, the second pixels being configured to generate the second color signal of a second luminance component that is a luminance component of narrow band illumination light having a wavelength band narrower than a wavelength band of the white illumination light, and the third pixels being configured to generate the third color signal of a color component different from the first and the second luminance components, a density of the first pixels being higher than each of a density of the second pixels and a density of the third pixels, the image processing apparatus comprising:
a specific frequency component extracting unit configured to extract a specific frequency component signal having a predetermined spatial frequency component, from a color signal of the first luminance component among the color signals of the color components generated by interpolation; and
a specific frequency component addition unit configured to add the specific frequency component signal extracted by the specific frequency component extracting unit to a color signal of a color component different from the first luminance component determined depending on an imaging method by the white illumination light or an imaging method by the narrow band illumination light.

2. The image processing apparatus according to claim 1, wherein the specific frequency component extracting unit comprises a filter processing unit configured to extract, by a band-pass filter or a high-pass filter having predetermined filter frequency characteristics, a response signal in accordance with the predetermined filter frequency characteristics.

3. The image processing apparatus according to claim 2, wherein interpolation filter processing is performed on the color signals of the color components generated by the interpolation, and
the specific frequency component signal has synthesized characteristics of the predetermined filter frequency characteristics in the filter processing unit and frequency characteristics after the interpolation filter processing.

4. The image processing apparatus according to claim 2, wherein the specific frequency component extracting unit comprises a clip processing unit configured to extract, as the specific frequency component signal, a signal having a specific amplitude in accordance with a structural object, from the response signal extracted by the filter processing unit.

5. The image processing apparatus according to claim 4, wherein the structural object is a blood vessel, and
the clip processing unit is configured to extract the specific frequency component signal from the extracted response signal based on a threshold in accordance with the blood vessel.

6. The image processing apparatus according to claim 4, wherein the clip processing unit is configured to switch clip processing between the imaging method by the white illumination light and the imaging method by the narrow band illumination light.

7. The image processing apparatus according to claim 1, further comprising:
an interpolation color difference calculating unit configured to:
interpolate the color signal of the first luminance component at a pixel position of the second pixels or the third pixels based on the first color signal surrounding the pixel position; and
calculate a difference between the color signal of the first luminance component generated by interpolation and the second color signal or the third color signal generated by the second pixels or the third pixels to generate a color difference signal;
a color difference interpolating unit configured to determine an interpolation direction based on the color difference signal generated by the interpolation color difference calculating unit, and interpolate a color difference signal missing at each pixel position; and
an image signal generating unit configured to generate a color signal of a color component different from the first luminance component based on the color difference signal after interpolation generated by the color difference interpolating unit and based on the color signal of the first luminance component generated by the interpolation color difference calculating unit.

8. A method for operating an image processing apparatus for interpolating a signal of a missing color component based on first, second, and third color signals respectively generated by first, second, and third pixels of an image sensor, to generate an image signal having color signals of color components, the first, second, and third pixels being arranged in a matrix, the first pixels being configured to generate the first color signal of a first luminance component that is a luminance component of white illumination light including red wavelength band light, green wavelength band light, and blue wavelength band light, the second pixels being configured to generate the second color signal of a second luminance component that is a luminance component of narrow band illumination light having a wavelength band narrower than a wavelength band of the white illumination light, and the third pixels being configured to generate the third color signal of a color component different from the first and the second luminance components, a density of the first pixels being higher than each of a density of the second pixels and a density of the third pixels, the method comprising:
extracting, by a specific frequency component extracting unit, a specific frequency component signal having a predetermined spatial frequency component, from a color signal of the first luminance component among the color signals of the color components generated by interpolation; and
adding, by a specific frequency component addition unit, the specific frequency component signal extracted by the specific frequency component extracting unit to a color signal of a color component different from the first luminance component determined depending on an imaging method by the white illumination light or an imaging method by the narrow band illumination light.

9. A non-transitory computer-readable recording medium with an executable program stored thereon for operating an image processing apparatus for interpolating a signal of a missing color component based on first, second, and third color signals respectively generated by first, second, and third pixels of an image sensor, to generate an image signal having color signals of color components, the first, second, and third pixels being arranged in a matrix, the first pixels being configured to generate the first color signal of a first luminance component that is a luminance component of white illumination light including red wavelength band light, green wavelength band light, and blue wavelength band light, the second pixels being configured to generate the second color signal of a second luminance component that is a luminance component of narrow band illumination light having a wavelength band narrower than a wavelength band of the white illumination light, and the third pixels being configured to generate the third color signal of a color component different from the first and the second luminance components, a density of the first pixels being higher than each of a density of the second pixels and a density of the third pixels, the program causing the image processing apparatus to execute:
extracting, by a specific frequency component extracting unit, a specific frequency component signal having a predetermined spatial frequency component, from a color signal of the first luminance component among the color signals of the color components generated by interpolation; and
adding, by a specific frequency component addition unit, the specific frequency component signal extracted by the specific frequency component extracting unit to a color signal of a color component different from the first luminance component determined depending on an imaging method by the white illumination light or an imaging method by the narrow band illumination light.

10. An endoscope device, comprising:
a light source unit configured to emit one of white illumination light and narrow band illumination light, the white illumination light including red wavelength band light, green wavelength band light, and blue wavelength band light, the narrow band illumination light having a wavelength band narrower than a wavelength band of the white illumination light;
an image sensor in which first, second, and third pixels are arranged in a matrix, the first pixels being configured to generate a first color signal of a first luminance component that is a luminance component of the white illumination light, the second pixels being configured to generate a second color signal of a second luminance component that is a luminance component of the narrow band illumination light, and the third pixels being configured to generate a third color signal of a color component different from the first and the second luminance components, a density of the first pixels being higher than each of a density of the second pixels and a density of the third pixels; and
the image processing apparatus according to claim 1.

* * * * *